United States Patent [19]

Hubbell et al.

[11] Patent Number: 5,330,911
[45] Date of Patent: * Jul. 19, 1994

[54] SURFACES HAVING DESIRABLE CELL ADHESIVE EFFECTS

[75] Inventors: Jeffrey A. Hubbell; Stephen P. Massia; Neil P. Desai, all of Austin, Tex.

[73] Assignee: Board of Regents, The University of Texas System, Austin, Tex.

[*] Notice: The portion of the term of this patent subsequent to Jan. 11, 2011 has been disclaimed.

[21] Appl. No.: 527,198

[22] Filed: May 21, 1990

Related U.S. Application Data

[63] Continuation-in-part of Ser. No. 414,144, Sep. 28, 1989, Pat. No. 5,278,063.

[51] Int. Cl.$^5$ .......................... C12N 5/06; C07K 5/10; C07K 7/06
[52] U.S. Cl. ...................... 435/240.243; 435/240.23; 530/329; 530/330
[58] Field of Search ................. 435/240.23, 240.243; 530/329, 330

[56] References Cited

U.S. PATENT DOCUMENTS 4,614,517  9/1986  Ruoslahti et al. ................. 530/330
5,092,885  3/1992  Yamada et al. ...................... 623/11

FOREIGN PATENT DOCUMENTS

WO8801279  2/1988  PCT Int'l Appl.

OTHER PUBLICATIONS

Burridge, et al.; Annual Review of Cell Biology, vol. 4, pp. 487–525; 1988.
Raja et al. "Preparation and Use of Synthetic Cell Culture Surfaces" J. Biological Chemistry, vol. 261, No. 18, pp. 8505–8513 1986.
Brandley, et al. Covalent Attachment of an ARG—GLY–ASP Sequence . . . Analytical Biochemistry vol. 172 pp. 270–278 1988.
Nilsson, et al. Immobilization of Enzymes and Affinity
(List continued on next page.)

*Primary Examiner*—George C. Elliott
*Attorney, Agent, or Firm*—Arnold, White & Durkee

[57] ABSTRACT

An absorbed protein-independent cell-adhesive surface is disclosed. The treated surface comprises a chemically derivatized material to which small peptides, having less than 12 amino acid residues and including YIGSR, RGD or REDV amino acid sequence are covalently linked to. The peptides of the present invention include a terminal glycine amino acid. Tresyl chloride activation of surface hydroxyl moieties provides the active surface sites by which a terminal glycine arm of a selected peptide attaches to form covalent bonds between the substrate and peptide. Peptides high with cell adhesive properties are bound in high efficiency.

By way of example, surfaces which may be used in conjunction with the present invention include polymer, metal, and ceramic surfaces. The most preferred polymer surfaces include PHEMA and PET polymer surfaces, with the most preferred glass surfaces being glycophase glass.

The present methods also include a pretreatment method which provides hydroxyl moieties to surfaces devoid of readily available hydroxyl moieties. The pretreatment, by way of example, comprises immersion of the surface in a mixture of formaldehyde and acetic acid.

Methods of preparing the treated surfaces are also included in the present invention.

Also included are surface-treated biomedical implant devices and cell culturing devices. The treated surface promotes an enhanced rate and an enhanced amount of cell adhesion to the surface, independent of media serum concentrations or other absorbed proteins. The treated surfaces of the present invention are thermally stable, reusable, peptide efficient (attached to surface only) and resistant to cell proteolysis.

The invention further concerns polymeric substrates with a surface having physically interpenetrating water-soluble polymer chains, and methods for production thereof.

57 Claims, 17 Drawing Sheets

OTHER PUBLICATIONS

Ligands . . . Biochem. Biophys. Res. Comm. vol. 102 No. 1 pp. 449–457 1981.
Graf, et al. A Pentapeptide from the Laminin B1 Chain . . . Biochemistry vol. 26 No. 22 pp. 6896–6900 1987.
Humphries, et al. Identification of an Alternatively Spliced Site . . . J. Cell Biology vol. 103 No. 6 Pt. 2 pp. 2637–2647 1986.
Tashiro, et al., A Synthetic Peptide Containing the IKVAV Sequence . . . J. Biological Chemistry vol. 264 No. 27, pp. 16,174–16,182 1989.
Kleinman, et al. Identification of a Second Active Site in Laminin . . . Arch. Biochem. Biophys. vol. 272, No. 1, pp. 39–45 1989.
Jaffe et al., "Culture of Human Endothelial Cells Derived from Umbilical Veins: Identification by Morphologic and Immunologic Criteria," J. Clinical Investigation, 52:2745–2756 (1973).
Dialog Search Reports (1990).
Woods et al., EMBO J., 5:665–670 (1986).
Streeter et al., J. Cell Biol., 105:507–515 (1987).
Paul et al., J. Appl. Pol. Sci., 20:609–625 (1976).
Mohr and Pommerening, *Affinity Chromotography: Practical and Theoretical Aspects*, Chap. 4 (1985).
Costello and McCarthy, Macromolecules, 20:2819–2828 (1987).
Tashiro et al., "A Synthetic Peptide Containing the IKVAV Sequence from the A Chain of Laminin Mediates Cell Attachment, Migration, and Neurite Outgrowth," J. Biol. Chem., 264(27):16174–16182 (1989).
Kleinman et al., "Identification of a Second Active Site in Laminin for Promotion of Cell Adhesion and Migration and Inhibition of *in Vivo* Melanoma Lung Colonization," Arch. of Biochem. & Biophys., 272(1):39–45 (1989).
Graf et al., "Identification of an Amino Acid Sequence in Laminin Mediating Cell Attachment, Chemotaxis, and Receptor Binding," Cell, 48:989–996 (1987).
Singer et al., J. Cell. Biol., 104:573–84 (1987).
Variani et al., In Vivo, 22:575–82 (1986).
Aubert et al., J. Biomed. Mater Res. 21:585–602 (1987).
Humphries et al., J. Cell Biol., 103:2637–2647 (1986).
Mugnai et al., J. Cell. Biol., 106:931 (1988).
Singer et al., J. Cell Biol., 106:2171 (1988).
Dejana et al., J. Cell. Biol., 104:1403 (Abstract( (1987).
Nilson and Mosbach, Biochem., & Biophy. Res. Comm., 102(1):449–457 (1981).
Grinnell, F., "Cellular Adhesiveness and Extracellular Substrate," Internatonal Review of Cytology, 53:67–149 (1978).
Couchman et al., J. Cell Biol., 93:402–410 (1982).
Pearlstein, E., Nature, 262:497–500 (1976).
Kleinman et al., Biochem. & Biophys. Res. Comm., 72:426–432 (1976).
Grinnell, F., Exp. Cell. Res., 97:265–274 (1976).
Grinnell, F., Exp. Cell. Res., 102:51–62 (1976).
Hynes et al., J. Cell. Biol., 95:369–377 (1982).
Pierschbacher et al., Nature, 309:30–33 (1984).
Pytela et al., Cell, 40:191–198 (1985).
Pytela et al., Proc. Natl. Acad. Sci., USA, 82: 5766–5770 (1985).
Fitzgerald et al., J. Biol. Chem., 260:11366–11374 (1985).
Ruoslahti et al., Science, 238:491–497 (1987).
Hynes, R. O., Cell, 48:549–554 (1987).
Cheresh, A., Proc. Natl. Acad. Sci., USA, 84:6471–6475 (1987).
Ohlson et al., FEBS Letters, 93:5–9 (1978).
PCT International Search Report, dated Jan. 21, 1991.
S. P. Massia et al.: "Covalent Surface immobilisation of arg-gly-as-p and tyr-ile-gly-ser-arg containing peptides to well defined cell-adhesive substrates", Dialog Information Service file 155: Medline 66–90/Nov., Medline Acc. No. 90343042.
S. P. Massia et al.: "Covalently attached GRGD on polymer surfaces promotes biospecific adhesion on mammalian cells", Dialog Information Service, file 5: Biosis Previews 69–92/Nov., BIOSIS Acc. No. 39130827.
Idemitsu Kosan K.K., Oct. 31, 1988, Dialog Information Service, file 351:WPI, WPI Acc. No. 88-351056/49.
Y. Yamada et al., Mar. 7, 1989, Dialog Information Service, file 351: WPI, WPI Acc. No. 89-1505g/20.
B. K, Brandley, et al., "Covalent attachment of an Arg-Gly-Asp sequence peptide to derivatizable polyacrylamid surface: support of fibro-blast adhesion and long-term growth", *Analytical Biochemistry*, 172:270–78, 1988.

OTHER PUBLICATIONS

K. Tashioro et al., "A synthetic peptide containg the IKVAV sequence from the A chain of Laminin mediates the cell attachment, migration and neurite outgrowth", Dialog Information Service, file 155: Medline 66-90/Nov., Medline Acc. No. 89380220.

M. J. Humphries et al.: "Identification of an alternatively spliced site in human plasma fibronectin that mediates celltypespecific adhesion", *J. Cell. Biol.*, 103(6) (2):2637-47, Dec. 1986.

Humphries et al, (1990) *In: Morphoregulatory Molecules*, Edelman, Cunningham and Thiery, eds., Chap. 6, p. 137.

Lark et al. (1985) *Federation Proceedings*, 44:394-403.

Streeter et al. (1987) *The Journal of Cell Biology*, 105:507-515.

Izzard et al. (1986) *Experimental Cell Research*, 165:320-336.

Woods et al. (1986) *The EMBO Journal*, 5(4):665-670.

Singer et al. (1987) *Journal of Cell Biology*, 104:573-584.

Hubbell, et al. (1991) Bio/Technology, 9:568-572, *Endothelial Cell-Selective Materials for Tissue Engineering in the Vascular Graft via a New Receptor*.

Massia et al. (1991) The Journal of Cell Biology, 114(5):1089-1100, *An RTD Spacing of 440nm is Sufficient for Integrin $\alpha_v\beta_3$-Mediated Fibroblast Spreading and 140 nm for Focal Contact and Stress Fiber Formation.*

USA Ser. No. 278,781 Aug. 17, 1988.

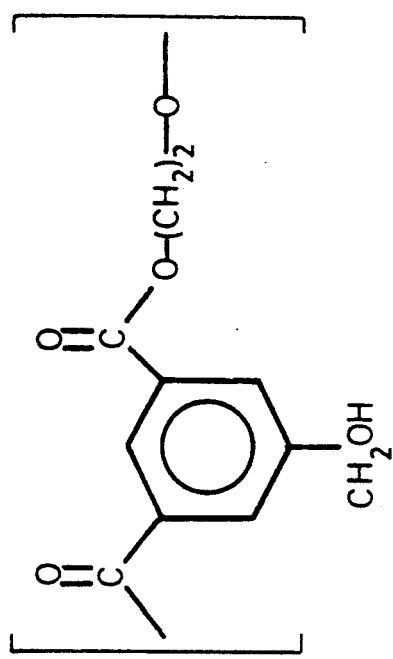
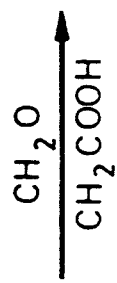
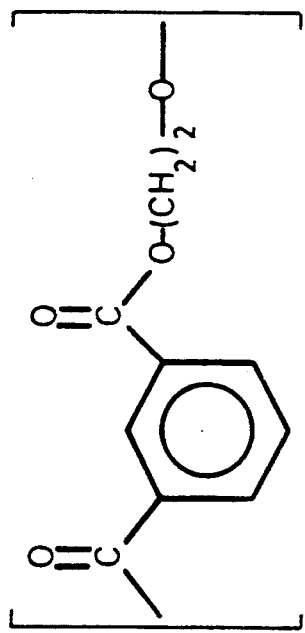
FIG. 1
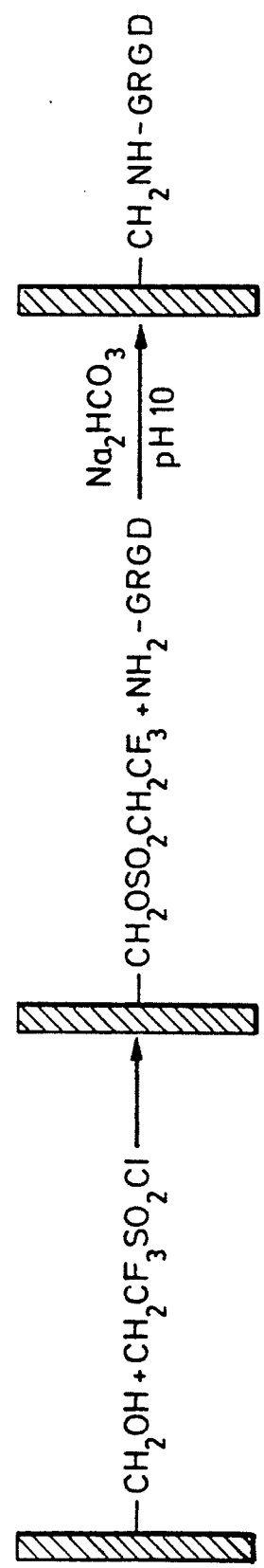
FIG. 2

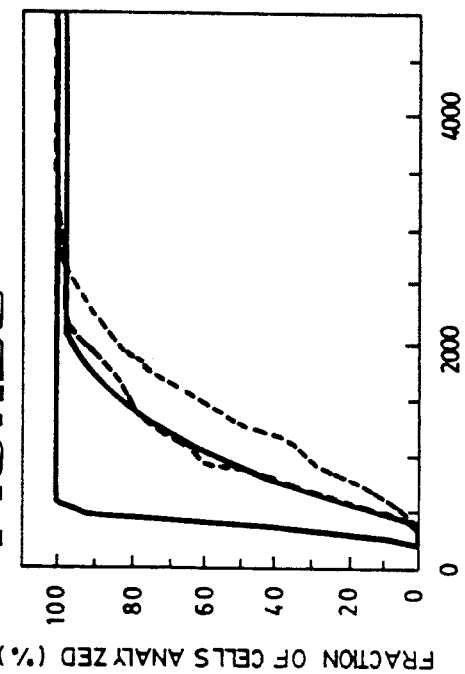
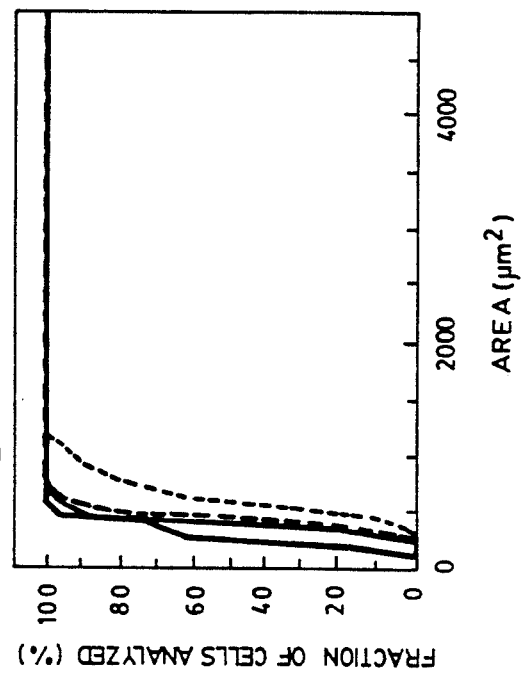
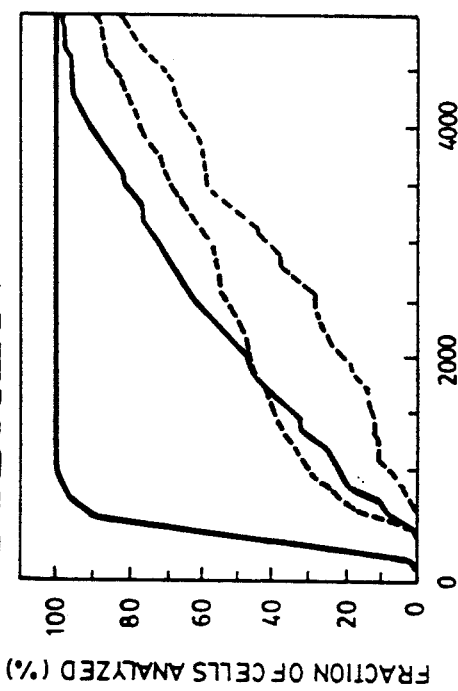
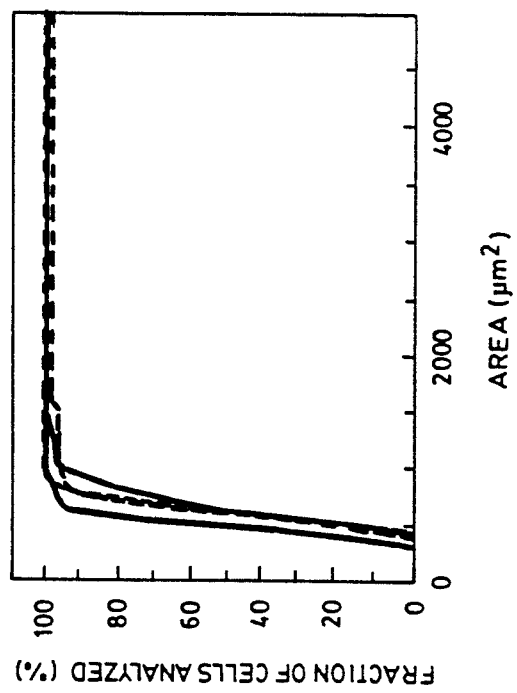

SURFACES HAVING DESIRABLE CELL ADHESIVE EFFECTS

The U.S. Government may have rights in the present invention as relevant developmental work was supported by National Science Foundation Grant CBT-881020268, and National Institutes of Health Grant HL-39714.

This is a continuation-in-part of U.S. Ser. No. 414 144 filed Sep. 28, 1989 now U.S. Pat. No. 5,278,063 issued Jan. 11, 1994.

BACKGROUND OF THE INVENTION

1. Field of the Invention

The field of the present invention relates generally to the biospecific adhesion of cells to a surface. More specifically, the invention relates to the chemical modification of a surface and the covalent attachment thereto of small peptides to promote cell adhesion. Even more particularly, the surface may comprise a ceramic, a metal or a polymer. The small peptides include a minimal cell receptor recognition amino acid sequence which promotes cell adhesion and is common to a variety of cell adhesion molecules. The surfaces and methods of the present invention thus relate to cell adhesion techniques which are independent of culture media serum composition and adsorbed surface proteins.

Moreover, the field of the present invention relates to the modification of polymeric materials by a solution processing technique to render the surfaces extremely nonadhesive to cells. Such surfaces have important applications in biomedicine and biotechnology. Furthermore, the field relates to the attachment of cell adhesion peptides to these nonadhesive surfaces to obtain surfaces that are cell adhesive and have the particular advantage of being specifically adhesive for certain cell types but not for other cell types.

2. Description of the Related Art

The interaction of cells with extracellular matrix in vivo is involved in a number of important biological processes, such as the regulation of cellular growth, migration, and differentiation. The role of eukaryotic cell adhesion in culture largely dictates the success of a particular cell culture effort or endeavor. Adhesion, spreading, and contraction on solid substances are prerequisites for growth of normal anchorage dependent cells in vitro (1, 2). This cellular bioadhesion is affected by several factors, including the particular type of cell, the cell culture media used, and the particular surface upon which the cells are cultured.

Many mammalian cells are cultured on polymer surfaces. Nearly all mammalian cell adhesion to synthetic polymer surfaces is controlled by adsorbed proteins and is receptor mediated. Fibronectin (FN), was the first cell adhesion molecule (CAM) that was shown to be involved in the adhesion of some avian and mammalian cell types to extracellular substrates (3, 4). FN is commonly provided to the in vitro environment through the addition of serum, in a form known as cold-insoluble globulin (CIg). For normal attachment and spreading of cells to occur, it was found that CIg had to be adsorbed to the culture surface (5, 6).

FN consists of several protease-resistant domains, each of which contain specific binding sites for other extra cellular molecules and for the cell surface (7). The cell attachment activity has been localized to a tripeptide sequence (RGD), located in the cell binding domain of FN as well as in several other CAMs (8). Substrate-bound, RGD-containing peptide, directly adsorbed to the substrate, or peptide cross-linked to adsorbed-albumin or IgG, was found to promote fibroblast attachment and spreading. This attachment and spreading activity was found to be readily inhibited by the addition of soluble RGD-containing peptides to the medium (8).

Affinity chromatography of cellular extracts on cell attachment-promoting FN fragments combined with specific elution utilizing synthetic RGD-containing peptides yielded a receptor with two 140 kD subunits (9). The mammalian FN receptor and other RGD directed receptors are typically heterodimers of two subunits, alpha and beta (10). Families of these receptors consist of members with similar beta subunits, whereas the alpha subunits are more distinct and restrict the receptor's affinity to one or a few CAMs (11). Collectively, these structurally and functionally related receptor families are known as the integrin superfamily (12, 13).

A basic understanding of the molecular mechanisms underlying the process of cell adhesion has thus developed regarding the role of the cell culture substrates and other surfaces in promoting cell adhesion. Basically, after a protein solution is placed on a culture substrate, proteins are immediately adsorbed to the surface. If there are receptors for some of these adsorbed proteins on the cell surface, and if the conformation of the adsorbed protein is not so extensively altered by adsorption as to destroy the high ligand-receptor affinity, then cell adhesion to the culture substrate and cell spreading can result.

If the cells are seeded on a substrate in the absence of adsorbed proteins, then the proteins on the cell surface may directly adsorb to the surface and the cell will, provided favorable conditions, secrete its own proteins toward the surface in the form of an extracellular matrix. However, if the substrate does not support protein adsorption, or if it supports high affinity adsorption of a protein for which there is not a cell-surface receptor, then the substrate will not support cell adhesion. In no case has the cell in culture been found to actually touch the surface except through these intermediate adsorbed proteins.

Some investigators who study short-term cell adhesion have proposed the use of substrate treating systems which promote cell adhesion wherein particular peptides are adsorbed to a polymer surface. For example, Singer, et al. proposed the adsorption of a 13-mer peptide containing the RGD sequence onto a polymer substrate to promote cell adhesion (14). However, peptides of this length have been found to be highly susceptible to degradation at high temperatures and to the proteolytic action of the cultured cells themselves. Additionally, peptides adsorbed to a surface are subject to desorption upon repeated use. Thus, surfaces with long amino acid residue peptides absorbed thereto have been found to be unstable and thus unsuitable in preparing reusable cell culture substrates.

An alternative approach in promoting cell adhesion is through chemical modification of the surface to facilitate the adsorption and attachment of protein and peptides to the substrate. However, present technology for chemical modification of substrates is particularly nonspecific and empirical. For example, treatment of polymer surfaces with various radio frequency plasma discharges, both polymerizing and nonpolymerizing, has been proposed. Alternative approaches of surface acid treatment or surface incorporation of charged groups have also been described. However, these various surface treatments alter only the pattern of protein adsorption on the culture surface, which in turn functions to modify the cells' characteristic adhesion and spreading behavior. Thus, the protein and peptide surface adsorption and desorption problems still remain, limiting the reusability of culture plates and other surfaces so treated.

An alternative to surface adsorption of peptides to promote cell adhesion has been to instead chemically attach peptides to a surface. For example, the method of polymer surface chemical modification was employed by Brandley, et al., (1988) (*Analyt. Biochem.* 172: 270), who proposed the inclusion of a 9-mer peptide in a polymer substrate to promote cell adhesion (Id.). While enhanced cell adhesion was attained using the Brandley technique, the method required similar concentrations of peptide to promote the same level of cell adhesion observed in the adsorbed peptide systems. For example, FIG. 1 of Brandley shows surface concentrations of peptide on the average of about 6 nanomoles per square centimeter (Brandley, at pg. 275). These high peptide concentrations suggest the Brandley method does not control for the inclusion of peptide at the polymer surface only, but instead permits the incorporation of peptide throughout the bulk of the polymer. Given that synthetic peptides cost about $5,000 per gram, this method would not facilitate the economical preparation of cell culture substrates commercially.

Thus, a need still exists in the art for an economical system of preparing thermally stable, peptide-coated surfaces with cell adhesion promoting characteristics which are resistant to the desorptive effects of repeated usage and proteolysis by cellular proteases or proteases added to remove cells. A more commercially feasible and economical system would be substantially more peptide-efficient than those proposed by Brandley and others of skill in the art of cell culture and polymer chemistry.

Currently used biomedical polymers in applications involving blood contact have not proved to be sufficiently nonthrombogenic to be useful in small diameter vascular grafts. Adhesion of platelets and other blood cells is the main cause of low patency of small diameter grafts, and an aspect of the present embodiment is to reduce the interactions of blood components with biomedical polymers. Because the adhesion of platelets, white blood cells, fibroblasts, etc. is mediated by the adsorption of proteins to the polymer surface, an approach was adopted which reduced the interaction of proteins with these polymers.

Polyethylene oxide (PEO) surfaces have been observed to resist the adsorption of plasma proteins as a result of their strong hydrophilicity, chain mobility and lack of ionic charge. Several groups have used PEO or PEG (polyethylene glycol) as a modifier in a quest to obtain a biocompatible or nonadhesive surface. Different approaches have been used to modify polymer surfaces with PEO. Among them are those techniques that involve covalent grafting of PEO to a base polymer such a PET, a polyurethane, or polyvinyl alcohol, polymerization of a monomer having a pendant PEO chain, incorporation of PEO into a base polymer by block copolymerization, or direct adsorption of PEO-containing surfactants which are typically block copolymers of the AB or ABA type where one of the blocks is a PEO. Most of these techniques have utilized PEO of relatively low molecular weights (less than 5000 daltons) and only a few have used significantly higher molecular weights.

Although some of the above described techniques work reasonably well in reducing cellular interactions at the surfaces of the modified polymers, most of them require multiple stages to obtain the necessary surface modification. Furthermore, they are limited by the structure and availability of labile chemical moieties on the base polymer surface and are in many cases, specific for modification of the base polymers.

The present invention relates to a technique incorporating PEO and other water-soluble polymers (WSP) into the surface of a base polymer (BP).

The following abbreviations are used by Applicants throughout the application:

A=Ala (alanine)
C=Cys (cysteine)
D=Asp (aspattic acid)
E=Glu (glutamic acid)
F=Phe (phenylalanine)
G=Gly (glycine)
I=Ile (isoleucine)
K=Lys (lysine)
P=Pro (proline)
R=Arg (arginine)
S=Set (serine)
V=Val (valine)
Y=Tyr (tyrosine)
BP=base polymer
CAM=Cellular adhesion molecule
CFN=cellular fibronectins
Cig=cold-insoluble globulin
DIFW=deionized and filtered water
FC=focal contacts
FEP=fluorinated ethylene polymers
fg=fibrinogen
FN=fibronectin
GREDV=glycine, arginine, glutamic acid, aspartic acid, valine or Gly-Arg-Glu-Asp-Val
GRGD=amino acid sequence glycine, arginine, glycine, aspartic acid; or Gly-Arg-Gly-Asp
HFF=human foreskin fibroblast cells
HVSMC=human vascular smooth muscle cells
kD=kilodalton
mer=amino acid residue
nm=nanomolar
PAE=porcine aortic endothelial (cells)
PBS=phosphate buffered saline
PDMS=poly(dimethyl siloxane)
PEG=polyethylene glycol
PELL=polyurethane (pellethane)
PEO=polyethylene oxide
PEOX=polyethyloxazoline
PET=polyethylene terephthalate
PFN=plasma fibronectins
PHEMA=poly(hydroxyethyl methacrylate)
PIPN=physical interpenetrating network
Plt=human blood platelets
PMMA=polymethylmethacrylate
Prestim Plt=human blood platelets prestimulated with 5 μm adenosine diphosphate
PTFE=poly(tetrafluoroethylene)
PVP=polyvinylpyrrolidone
REDV=arginine, glutamic acid, aspartic acid, valine or Arg-Glu-Asp-Val RGD = amino acid sequence arginine, glycine, aspartic acid, or Arg-Gly-Asp
SAM = surface (or substrate) adhesion molecule
TFAA = trifluoroacetic acid
THF = tetrahydrofuran
$\mu$g = micrograms
$\mu$l = microliter
WSP water soluble polymer
YIGSR = tyrosine, isoleucine, glycine serine, arginine, or Tyr-Ile-Gly-Ser-Arg

SUMMARY OF THE INVENTION

The present invention features a new process by which surfaces may be modified to yield proteolytically stable, reusable surfaces which promote the amount of and enhance the rate of receptor mediated cell adhesion. The specifically directed and controlled chemical processes herein disclosed provide for the chemical attachment of peptides at the surface of a flask or other device without diffusion of the peptide throughout the bulk of the material treated. Thus, the disclosed methods provide a surprisingly enhanced cell adhesion promoting surface with the use of only a fraction of the peptide required by formerly proposed methods. The peptides are chemically attached to a surface, and thus avoid the desorption problems which plagued surface peptide-adsorbed systems of the past. These advantages are accomplished through the chemical attachment of small peptides, for example, those having less than 12 amino acid residues, at only the surface of the substrate.

An additional feature of the present invention lies in that the process provides for the use of cell adhesion molecule fragments, rather than whole surface adhesion molecule (SAM) proteins. The acronyms SAM and CAM are used interchangeably to denote surface, substrate or cell adhesion molecules that are proteins which interact with extracellular matrix components through a specific binding domain to promote specific domain-mediated adhesion of cell receptors (i.e., the cells). SAMs are a family of proteins that include fibronectin, vibronectin, thrombospondin, laminin, and other proteins. Grafting of small peptide fragments provides a further advantage in that surfaces so treated are less subject to denaturation and proteolytic degradation than surfaces grafted with whole proteins or larger peptides.

A further feature of the present invention is that it provides a more efficient surface modification system. For example, Applicants are able to produce a derivatized surface with maximal cell adhesion properties using only 1/500th the amount of peptide of formally proposed chemical grafting methods. For example, Brandley, et al. employed a method which yielded on the average of 6 nanomoles/cm$^2$ (6,000 picomoles/cm$^2$) peptide surface concentration (Brandley, et al., pg. 274, Table 1). In contrast, Applicants have demonstrated enhancement of cell adhesion with a surface peptide concentration of as little as 0.001 nanomoles/cm$^2$ (a six million fold improvement). Applicants were able to omit a significant amount of the surface peptide in the process of chemically binding a peptide to a surface, and were able to achieve such without a loss in cell adhesive promoting activity.

An additional feature of the disclosed surface modification techniques is that they provide a novel approach for promoting receptor-mediated cell attachment independent of adsorbed serum components. The present invention provides a method for the treatment of surfaces which is effective in promoting the adhesion of any species and type of cell, including for example, porcine, murine and human cells. Types of cells which have already been successfully cultured on the treated surfaces include aortic, foreskin fibroblast and 3T3 fibroblast cells (ATCC # CRL1658) and vascular endothelial cells.

The present invention also features adaptability of use with a wide variety of small peptides. While numerous small peptides may be used in conjunction with the present invention, the most preferred small peptides include those with less than 12 amino acid residues (12 mer). More preferably, these peptides contain 3-9 amino acid residues (3-9 mer). The most preferred peptides have either 6 amino acid residues (6 mer) or 4 amino acid residues (4 mer). The number of amino acid residues in a peptide are often denoted herein by such nomenclature (e.g., 6 mer, 4 mer, etc.).

These small peptides are further described as including a minimal cell-surface receptor recognition sequence, for example, RGD, YIGSR, or REDV. This sequence permits the cell receptor mediated support of cells to a treated surface. By way of example, the most preferred peptides which include the about minimal cell surface receptor recognition sequences include the GRGD (Gly-Arg-Gly-Asp), GYIGSRY (Gly-Tyr-Ile-Gly-Ser-Arg-Tyr), GYIGSR (Gly-Tyr-Ile-Gly-Ser-Arg), GRGDY (Gly-Arg-Gly-Asp-Tyr), YIGSR (Tyr-Ile-Gly-Ser-Arg), RGD (Gly-Arg-Asp), REDV (Arg-Glu-Asp-Val), GREDV (Gly-Arg-Glu-Asp,Val), GREDVY (Gly-Arg-Glu-Asp-Val-Tyr), RGDS (Arg-Gly-Asp-Ser), GRGDS (Gly-Arg-Gly-Asp-Ser), RGDF (Arg-Gly-Asp-Phe), GRGDF (Gly-Arg-Gly-Asp-Phe), PDSGR (Pro-Asp-Ser-Gly-Arg), GPDSGR (Gly-Pro-Asp-Ser-Gly-Arg), GPDSGRY (Gly-Pro-Asp-Ser-Gly-Arg-Tyr), IKVAVC (Ile-Lys-Val-Ala-Val-Cys), GIKVAV (Gly-Ile-Lys-Val-Ala-Val), IKVAVY (Ile-Lys-Val-Ala-Val-Tyr), GIKVAVY (Gly-Ile-Lys-Val-Ala-Val-Tyr) amino acid sequences. These fragments contain either the cell attachment sequence of many surface adhesion molecules (RGD) or one of the cell attachment sequences of laminin (YIGSR and PDSGR), a particular surface adhesion protein, or the cell adhesion molecule fibronectin (REDV). The IKVAV peptide from laminin is also useful for particular cells. These most preferred peptides may further include a C-terminal Y for radioiodination. The N-terminal G is used as a spacer with the particular peptide between the adhesive peptide and the surface. The small peptides are used to provide cell receptor recognition sites required for cell adhesion on the treated surface.

While a surface concentration of peptides of at least 0.001 picomole/cm$^2$ is sufficient to enhance the cell adhesive characteristics of a surface, a preferred range of peptide surface concentration is between about 0.001 to 100 picomoles/cm$^2$. A more preferred range of peptide surface concentration is 0.5 to 20 picomoles/cm$^2$. The most preferred peptide surface concentration of the present invention is about 12 picomoles/cm$^2$.

Conventional methodologies rely upon direct adsorption of the CAM or the peptide to the surface, or adsorption of non-CAM proteins followed by cross-linking of the peptides to the adsorbed proteins, thus allowing for desorption of these components into the culture media. The present invention provides the further advantage of avoiding this problem of protein desorption by chemically bonding the peptide through covalent bonds to hydroxyl or other reactive moieties of the desired substrate.

There are many situations in the use of biomedical implants where it is desirable that the surrounding cells in the tissues adhere to and spread upon (integrate with) the implant surface. The present invention provides a method for surface modification to obtain such desired implant integration within the host. The present invention further features a method for reducing the incidence of infection attendant to the in vivo implant of biomedical devices. A major risk associated with implantation of biomedical devices has been infection. The lack of a continuous protective layer between the device and the biological tissue opportunizes the entry of bacteria and other infectious agents into the tissue. With the enhanced cell adhesion promoting surface as part of the device, such undesirous side effects will be minimized, as a continuous protective cell covering is provided, closing the potential entry of infectious agents.

Furthermore, there are many situations in the use of biomedical implants that only specific cells from the surrounding tissues attach to the implant surface. For example, in vascular graft technology, it is desirable that endothelial cells attach to the implant so that it will look like the natural blood vessel wall, which is lined with endothelial cells. However, platelets also attach and lead to clotting, and fibroblasts and smooth muscle cells also infiltrate from the tissues, leading to a very detrimental thickening of the tissue layers within the vascular graft. Thus, it would be advantageous to utilize a material to which platelets do not attach and to which only endothelial cells attach. The present invention provides, as a surprising advantage over adsorbing peptides to surfaces, this feature of cell-type specificity.

Additionally, the long-term stability of the disclosed treated surface method makes the system ideal in preparing various biomedical implants for extended term body emplacement. For example, in use with nerve growth guides and indwelling catheters. The surface modification system of the present invention also provides new avenues for mammalian cell bioreactor design, since it provides a stable integral surface component which supports cell adhesion independent of media CAMs. Such substrates provide the further advantage of permitting the use of serum-free media which are deficient in cell adhesion molecules.

The chemistry of the present invention is directly applicable to any material with surface hydroxyl moieties or other surface reactive groups to which such moieties can be added. Most other surface treatments to enhance cell adhesion do so by the enhancement of protein absorption. The peptide grafting approach of the present invention eliminates the requirement for absorbed proteins completely, as the cell has receptors for the surface-coupled synthetic peptides. These covalently bound minimal sequences are much more stable to cellular proteolysis and thermal degradation than adsorbed cell adhesion proteins or adsorbed proteins conjugated with adhesion peptides, since desorption is eliminated and the active groups (e.g. RGD, YIGSR, PDSGR, IKVAV or REDV sequence) are not as exposed to soluble proteases.

While a variety of chemical methods exist by which the present surfaces may be prepared, the various approaches fall into the general class of surface activation, via modification of a nucleophile, such as an amine or hydroxyl, followed by coupling to the peptides, via another nucleophile such as an amine or hydroxyl or thiol (23). By way of example, the activation of surface hydroxyl groups may be accomplished through treatment with agents such as tresyl chloride, glutaraldehyde, cyanuric chloride, sulfonyl chlorides, cyanogen bromide; surface hydroxyls may be added via benzoin with potassium tert-butoxide in dimethyl sulfoxide. Treatment with these particular surface activators is followed by a procedure by which a peptide is covalently linked to the hydroxyl group. Additionally, the present invention may be practiced through the production of active carboxyl groups on the surface by using, for example, succinic anhydride. The exposed surface is then rinsed and coupled with peptide.

By way of example, biomedical implants which would benefit from the inclusion of the present surface peptide treatment include penile, heart, vaginal, and hip implants; catheters; artificial veins or arteries, artificial tendons and, ligaments; artificial bone screws, bone plates, bone fragments and bone joints; artificial skin; nerve growth guides; and intraocular lenses and the like. By way of example, materials used as cell and tissue culture substrates which profit from the present surface peptide treatment include tissue culture flasks, petri dishes, microcarrier beads, porous macrocarriers, fibers, hollow fibers, monolith supports, and roller bottles.

The disclosed methods may be used in the derivatization of any surface to which enhanced cell adhesion is desired. By way of example and not limitation, these surfaces include metal, ceramic or polymer surfaces. A preferred embodiment of the invention is directed to the derivatization of polymer surfaces. While any polymer surface may be derivatized using the proposed methods, particular exemplary polymer surfaces most preferably include poly(hydroxyethyl methacrylate) (PHEMA), poly(ethylene terephthalate) (PET), poly(tetrafluoroethylene) (PTFE), fluorinated ethylene (FEP), poly(dimethyl siloxane) (PDMS) and other silicone rubber surfaces. PET, otherwise known as Dacron, is a polyester frequently used for biomedical implants. PTFE is otherwise known as Teflon. Most preferred polymeric matrix of the present invention comprises poly(hydroxyethyl methacrylate) (PHEMA).

The PHEMA polymeric matrix comprises a gel-like matrix having about a 45% water composition, and was, prior to the disclosure of the present invention, unable to support cell adhesion.

Use of peptides in conjunction with other high-water polyacrylamide gel matrixes is much less peptide-efficient compared to such use with polymers of lower water content. Highly hydrated gels are highly permeable to peptides and thus facilitates the substantial and indiscriminant diffusion of small peptides into the bulk of the polymer. These highly hydrated polymers have been used for protein electrophoresis, demonstrating that they are even permeable to whole proteins, which are very large molecules (21). Polymer gels comprising polyacrylamide usually include at least about 90% water, and, thus would be unsuitable in the practice of the present invention.

Another preferred embodiment of the invention is directed to the derivatization of a particular ceramic, glycophase glass (glycerol propylsilane bonded glass). By way of example, a preferred metal to be used with the described process is titanium.

The present invention also includes methods of enhancing cell adhesion to a surface comprising first activating the surface, coupling a peptide to the activated surface, and then plating mammalian cells on the peptide derivatized surface, wherein the preferred peptide is smaller than a 12 met. The process whereby the peptide is coupled to any activated surface most preferably comprises exposing an activated surface to a solution containing a sufficient amount of the peptides described above (having cell-adhesive characteristics). While any concentration of peptide solution of at least about 10 ng/ml would produce equal results in the present coupling process, solutions between about 10 ng/ml peptide and 100 ug/ml peptide are also suitable. Most preferably, the process includes a peptide solution having a concentration of 10 ng/ml peptide. In one preferred embodiment of the invention, the peptide of the peptide solution includes the amino acid sequence arginine-glycine-asparagine (RGD). In another preferred embodiment of the invention, the peptide of the peptide solution includes YIGSR. In still another preferred embodiment of the invention, the peptide of the peptide solution includes PDSGR, IKVAV, REDV or RGDF. A most preferred peptide to be used in the method of the present invention comprises a peptide sequence selected from the group consisting of GRGD, RGDY, GRGDY, GYIGSR, GYIGSRY, YIGSR, RGDS, REDV, GREDV, GREDVY, RGDF, GRGDF, PDSGR, GPDSGR, GPDSGRY, IKVAV, GIKVAV, IKVAVY, and GIKVAVY. These peptides are most preferably used in the derivatization of polymer surfaces, such as PET polymer and PHEMA polymer, or glass surfaces, such as glycophase glass. However, any peptide which includes an amino acid sequence capable of supporting cell receptor recognition may be used in conjunction with the present invention.

Applications of the bioactive cell adhesive peptide grafting approach to enhance cell adhesion include the following uses:

1. For laboratory scale tissue and cell culture of anchorage dependent cells and cell lines This approach may be useful in the treatment of laboratory glassware and plasticware used as cell culture substrates, such as tissue-culture flasks and Petri dishes. It would be useful for animal, insect, and plant cells and tissues, as all utilize essentially the same molecular biology for adhesion.
2. For large scale tissue and cell culture. The approach may be useful in the treatment of microcarriers, porous macrocarriers, hollow fibers, monolith supports, and roller bottles.
3. For the interior of implantable artificial vascular grafts to promote the endothelialization of these surfaces.
4. For the exterior and anastamotic regions (ends) of vascular grafts to promote integration into the tissues.
5. For other implantable devices where integration with the tissues is desirable, such as artificial tendons, ligaments, bone screws and plates, bone fragments, joints, and skin.
6. For the treatment of sutures to promote adhesion with and integration to the tissues.
7. For the promotion of directional growth or migration of cells or tissues, this approach may be useful when the peptides are grafted to the surface with a gradient of surface concentration. An example where this may be useful is in nerve growth guides for peripheral nerve regeneration.
8. For use in research. The present systems allow for the study of cell adhesion in the presence of serum without the confusion of the effects of protein adsorption. Thus, background levels in the test system remain low. Additionally, the present methods control for the amount of peptide which gets coupled to a surface, which is also important in studying cell adhesion.

Surfaces modified to resist cell adhesion prepared according to the present invention may be useful for:

1. Situations in biomedicine where cell attachment is detrimental, such as catheters, hemodialysis membranes, blood filters, intraoccular lenses, contact lenses, and
2. Situations in biotechnology where protein adsorption is detrimental, such as chromatography support columns.

BRIEF DESCRIPTION OF THE DRAWINGS

FIG. 1 shows the hydroxymethylation of PET films via electrophilic aromatic substitution. The reaction was carried out at room temperature with 18.5% formaldehyde (v/v) and 1M acetic acid.

FIG. 2 shows the tresyl activation and GRGD coupling to hydroxymethylated PET films. All reactions were performed at room temperature.

FIGS. 12A-D shows cumulative histograms showing the cell areas of HFFs on glycophase glass derivatized with GYIGSRY. Cells were suspended in either complete medium (12A), (12B), or serum-free medium containing albumin (12C), (12D), and inoculated on the substrates. (12A) and (12C) represent data collected on the YIGSR-derivatized glass, whereas (12B) and (12D) represent data collected on the nonadhesive control surfaces. The areas of individual cells were determined by phase contrast video microscopy coupled with digital image processing (12). Cell spreading was observed on the peptide-grafted surfaces, even in the absence of serum; there was no cell spreading on the ungrafted surfaces even with serum, and most of these cells were nonadherent. (At least 100 cells were analyzed at each time point to generate the cumulative data.) Lines: (solid line) 0 hours; (dotted line) 3 hours; (heavy dashed) 6 hours; and (light dashed) 9 hours). Midpoint cell area, with 50% of the cells above and 50% below for the various time points (in order): 12A: 0 hours; 505 $\mu m^2$; 3 hours, 2200 $\mu m^2$; 6 hours, 2333 $\mu m^2$; 9 hours, 3375 $\mu m2$; 12B: 340, 520, 486, 517; 12C: 517, 1045, 1033, 1400; 12D: 245, 306, 362, 514.

DETAILED DESCRIPTION OF THE PREFERRED EMBODIMENTS

Figure 3A:
FIGS. 3a and 3b shows adherent and spread 3T3 fibroblasts on (3a) GRGD coupled and (3b) untreated PET films. Arrows indicate individual cells that were scored as spread cells. (200X Hoffman illumination).

The present invention is related to surfaces having unique self-adhesive properties and methods of preparing treated surfaces which specifically enhance cell-surface adhesion thereto independent of separately adsorbed peptides and soluble media components. This methodology provides techniques for preparing various types of substrates which simplify optimization of culture systems and which also control the amount and rate of cell bioadhesion to surfaces of various materials. Moreover, materials having particular cell nonadhesive properties and methods for preparing such surfaces to reduce cell adhesion and protein adsorption are disclosed. These materials have important utility as nonadhesive surfaces and have particular advantages when modified with adhesion-promoting peptides.

More particularly, the surface modification techniques provide for the chemical grafting of peptides to a surface, the peptide comprising at least the minimal amino acid sequence included in a cell (surface) adhesion molecule, such as RGD in fibronectin, or YIGSR, IKVAV or PDSGR in laminin, REDV in some forms of fibronectin, or some other short peptide sequence related to or derived from the sequence of a protein involved in cell-surface or cell-cell adhesion. The terms "Cell Adhesion Molecule" (CAM) and "Substrate Adhesion Molecule" (SAM) are used interchangeably in describing the family of proteins and peptides found to facilitate cell receptor-mediated adhesion or attachment to a surface.

The present surface treatment methods comprise chemically activating a surface to expose reactive groups, rinsing the actuated surface, and then exposing the surface to a solution containing small peptides, for example, a peptide which includes the RGD, PDSGR, IKVAV, YIGSR, REDV, or other amino acid sequence which facilitates receptor mediated cell attachment having less than a total of 12 amino acid residues (12-mer). A covalent chemical bond attaches the terminal end of the peptide to a reactive moiety on the surface being treated. A variety of chemical methods exist by which a surface may be activated to expose reactive groups. One of these methods is by way of the tresyl activation. Other alternative chemistries which may be used in the practice of the present invention, by way of example include:

(1) Activation of the surface with glutaraldehyde: At temperatures between 0° C. and 80° C., treat the surface with an aqueous solution of 5% to 37% glutaraldehyde for about one hour. The glutaraldehyde will couple with any exposed nucleophilic groups, such as amines and hydroxyls. Rinse the surface with water, and treat the surface with a solution of peptide, between 10 ng/ml and 1 mg/ml. Nucleophilic groups on the peptide, such as thiols, amines, and hydroxyls, will be coupled to the surface-coupled glutaraldehyde function.

(2) Activation of the surface with cyanuric chloride: At temperatures between 0° C. and 80° C., treat the surface with a nonaqueous solution of about 5% cyanuric chloride for about one hour. The cyanuric chloride will couple with any exposed nucleophilic groups, such as amines and hydroxyls. Rinse the surface with dry solvent, and treat the surface with a solution of peptide, between 10 ng/ml and 1 mg/ml in a nonaqueous solvent, such as acetonitrile. Any nucleophilic groups on the peptide, such as thiols, amines, and hydroxyls, will be coupled to the surface-coupled cyanuric chloride function.

(3) Activation of the surface with other sulfonyl chlorides: Follow the procedure outlines in Example 3 using another member of the sulfonyl chloride family, such as tosyl chloride.

(4) Activation of the surface with cyanogen bromide: At temperatures about 20° C. or below, expose the surface to an aqueous solution of cyanogen bromide at pH 10-11 for about one hour. The cyanogen bromide will covalently couple and activate surface hydroxyl groups. Rinse the surface with water at pH 10-11, and couple with peptide between 10 ng/ml and 1 mg/ml in this same solution for about 1 hour. The peptide will couple to the cyanogen bromide groups via any amine functions on the peptide.

(5) Activation of the surface to produce active carbonyl-bearing esters, e.g. with succinic anhydride: At temperatures of about 20° C., expose the surface to a solution of succinic anhydride, whereupon that compound will react with surface hydroxyls and amine to produce esters and amides, respectively. Rinse the surface and couple with peptide between 10 ng/ml and 1 mg/ml for about 1 hour. The peptide will react with the activated surface via amine or hydroxyl groups.

(6) Preactivating a polymer by adding hydroxyls with benzoin dimethyl sulfoxide: Hydroxyl functions are added to poly(tetrafluoroethylene) (PTFE). As described by Costello and McCarthy, Surface-Selective Introduction of Specific Functionalities onto Poly(tetrafluoreoethylene), *Macromolecules* 20:2819-2828 (1987)). Benzoin is added to a solution of potassium tert-butoxide in dimethyl sulfoxide and placed in contact with the PTFE surface. The reaction is allowed to proceed at 50° C. for 1 hour. The material is removed and rinsed with tetrahydrofuran (THF). This intermediate surface is then treated with 1M borane in THF at room temperature for 12 hours. The surface is then treated with 1M NaOH containing 10% hydrogen peroxide at 0° C. for 3 hours, after which it is washed sequentially with dilute NaOH, water, dilute HCl, water, THF, and heptane. This produces a surface that is rich in hydroxyls and can subsequently be activated by any of the chemistries described above.

The most preferred method by which peptides are attached to a surface comprises surface activation of the surface, by a tresyl immobilization method, as described by Nilsson and Mosbach (1981) (*Biochem. Biophys. Res. Commun.*, 102: 449-457). Specifically, tresyl activation is a process wherein the surface is first immersed in 20 ml. dry ether containing about 40 µl 2,2,2-trifluoroethanesulfonyl chloride (tresyl chloride) and about 2 ml. triethylamine for about 15 minutes at room temperature. These activated surfaces were then rinsed with 0.2M sodium bicarbonate pH 10 buffer. The surfaces were then placed in the same buffer containing about 60-100 ng/ml of the peptide for about 20 hours at room temperature. Most preferably, the concentration of peptide solution is about 10 ng/ml. This incubation time allows for the coupling of the peptide to the surface hydroxyl groups. This particular embodiment of the invention is preferably used with the GRGD peptide.

The peptides couple to an activated surface most preferably by exposing the activated surface to a solution containing an appropriate amount of the desired peptide. While any concentration of peptide solution of at least about 10 ng/ml would produce equally satisfactory results, solutions containing between about 10 ng/ml peptide and 100 ug/ml peptide are preferred. Most preferably, a peptide solution of about 10 ng/ml peptide is used in the coupling process.

The treated surfaces produced by the disclosed methods are characterized by a peptide surface concentration of at least 0.001 picomole/cm$^2$. It is expected peptide surface concentrations of at least 0.001 picomole/cm$^2$ are sufficient to enhance the cell adhesive characteristics of a surface. A more preferred range of peptide surface concentration is between about 0.5 to 100 picomoles/cm$^2$. A most preferred range of peptide surface concentration is between about 0.5 to 20 picomoles/cm$^2$. The most preferred surface peptide concentration is about 12 picomoles/cm$^2$.

Where no surface hydroxyl moieties exist on the surface to be treated, the surface was pretreated. This pretreatment preferably comprised a surface hydroxylation procedure wherein an electrophilic aromatic substitution was employed to add hydroxyalkyl groups to a surface. A particularly preferred method of this pretreatment comprises immersing a surface in an about 18.5% (v/v) solution of formaldehyde and about 1M acetic acid for about 4 hours at room temperature. This procedure was used in the hydroxymethylation of a particularly preferred embodiment of the invention comprising a PET polymer surface. The hydroxylated surface was then tresyl activated with the attachment of peptides thereto as described above. Most preferably, the pretreatment method disclosed herein is used to prepare polymer surfaces, particularly PET polymer surfaces, with GRGD or GYIGSR peptides. Various other surface hydroxylations would be equally as useful for use in conjunction with other polymers or materials. Various other linking characteristics may also be used, where the N-terminal amine or another reactive group on the peptide is reacted with a group on the surface, perhaps with the use of some linker.

Any surface may be used in the practice of the present invention. By way of example, surfaces particularly suitable for use in the practice of the present invention comprise a ceramic, a metal, or a polymer surface. Most preferably, the present invention is used in the treatment of polymer surfaces and ceramic (glass) surfaces. By way of example, the polymer surfaces comprise poly(-hydroxyethyl methacrylate) (PHEMA), poly(ethylene terephthalate) (PET), poly(tetrafluoroethylene) (TPFE), fluorinated ethylene (FEP), poly(dimethyl siloxane) (PDMS) and other silicone rubbers. While a variety of glass surfaces may be treated with the proposed methods, the glass surface most preferred comprises glycerol propylsilane bonded glass (glycophase glass). A particularly preferred polymeric surface is one with a physical interpenetrating polymeric network of water-soluble polymer resisting cell adhesion without peptide substitution.

A minimal amino acid sequence included in many cell adhesion molecules is RGD (arginine-glycine-aspartic acid amino acid sequence), or YIGSR (tyrosine-isoleucine-glycine-serine-arginine) or REDV (arginine-glutamic acid-aspartic acid-valine). While any peptide containing a minimal amino acid sequence active in cell adhesion may be used in the practice of the present invention, those sequences most preferred comprise RGD, YIGSR, GRGD, GYIGSR, PDSGR, IKVAV, GRGDY, GYIGSRY, RGDY, YIGSRY, REDV, GREDV, RGDF and GRGDF.

In a particularly preferred embodiment of the present invention, the peptides GRGDY and GYIGSRY are chemically grafted to a surface of glycerol propylsilane bonded glass (glycophase glass) a specific type of ceramic. The C-terminal Y of these preferred peptides is included for radio iodination, the N-terminal G (glycine) is provided for use as a spacer with the particular peptide between the adhesive peptide and the surface. The small peptides are used to provide cell receptor recognition sites required for cell adhesion on the treated sequence.

In another particularly preferred embodiment of the present invention, the GRGD and GYIGSR peptides are used in the chemical derivatization of polymer surfaces. A most preferred embodiment of the present invention comprises a PHEMA or PET polymer surface derivatized with GRGD or GYIGSRY peptides. Another even more most preferred embodiment of the present invention comprises a PHEMA or PET polymer surface derivatized with GYIGSRY peptides.

A surface so treated to include covalently bound peptide provides mammalian cell receptor recognition sites which allow the cells to anchor to the substrate and grow independent of media serum content and surface adsorbed proteins. Thus, the present invention discloses methods which provide for receptor-mediated cell adhesion in the absence of any intermediate adsorbed protein, i.e., an entirely self sufficient cell adhesion and spreading supportive surface.

While any peptide fragment which includes the minimal amino acid sequence of the cell adhesion molecule may be used in the practice of the present invention, peptide fragments containing less than 12 amino acid residues (mer) are preferred. Peptide fragments having between about 3 and about 9 amino acid residues are more preferred. The most preferred peptides include either 4 or 6 amino acid residues. The length of the peptide fragment will affect the susceptibility of the peptide to degradation, and therefore, the shorter the fragment, the less peptide surface degradation would be expected.

The present invention further includes surface-treated biomedical implant devices and methods for preparing the same. Devices having such surface treatments enhance the amount and rate of cell adhesion, and thus the rate of tissue integration of the device in vivo. Enhanced cell adhesion and tissue integration act to minimize infection, as potential tissue ports of entry are "sealed" closed by a protective layer of cells.

Any device surface to which the described peptides may be chemically grafted can be treated with the described methods. By way of example, these device surfaces include those of penile, vaginal, heart and hip implants or replacements; catheters; artificial skin, veins and arteries; artificial tendons and ligaments; artificial bone screws, plates, fragments and joints; nerve growth guides; intraocular lenses and the like.

Since polyethylene oxide (PEO) surfaces have been shown to resist adsorption of proteins, PEO was incorporated to the surfaces of commonly used biomedical polymers such as polyethylene terephthalate (PET), pellethane (a commercial polyurethane, PELL) and polymethylmethacrylate (PMMA). A novel solution technique was used to incorporate PEO and other water-soluble polymers (WSP) such as polyvinylpyrrolidone (PVP) and polyethyl oxazoline (PEOX). The presence of PEO, PVP and PEOX on these surfaces was verified by using contact angle analysis and ESCA. The short-term blood compatibility on the modified polymers was studied in an in vitro parallel plate flow system used in conjunction with epifluorescence videomicroscopy that could be used to quantify adherent platelets on the polymer surfaces. It was found that the PEO modified surfaces showed a lower thrombogenicity over the respective control surfaces, with the PEO of molecular weight 18500 showing a much lower cellular response than the 5000 or the 100000 molecular weight PEO as well as the other water soluble polymers. Scanning electron microscopy was performed on these surfaces after blood flow and these tests showed similar results to the videomicroscopic analysis. Adhesion and spreading of human foreskin fibroblasts on the modified surfaces was used to test the effectiveness of PEO, PVP and PEOX in preventing cell adhesion. A dramatic response was obtained for the PEO 18500 modified surfaces in that, over the almost 30 days following the seeding of these cells, an extremely low adherence was obtained on the PEO 18500 modified surfaces whereas all the others reached confluency within five to ten days. These results, along with protein adsorption studies which showed a significant reduction in adsorbed protein only on the PEO 18500 modified surfaces, suggest that this molecular weight may be suitable in preventing protein adsorption and hence cellular interactions at the surface of the modified polymer. The PEO 5000 molecule may be too short to perform this function effectively and the PEO 100000 may be too long or bulky to be effectively incorporated into the base polymer surface. Both PVP and PEOX have amides in their repeat unit and this may serve as a potential interaction site leading to protein adsorption and cellular attachment. Thus a PEO molecule greater than 5000 and smaller than 100000 is usable to preclude protein and cellular adhesion to a bare polymer.

While these cell nonadhesion materials have utility on their own, they are also particularly useful when used as a base material to which adhesion-promoting peptides are attached. In this situation, proteins do not adsorb to the surface, and as such the only adhesion-promoting materials on the surface are those which were added chemically in the form of the peptide. This allows for cell-type specificity to be built into the surface by control of the particular peptide that is incorporated, modulation of the linking arm by which the peptide is attached to the surface, and modulation of the peptide surface density. Such specificity is not possible when the peptide is adsorbed to the surface, as proteins would also adsorb, leading to multiple adhesion signals.

Applicants' evidentiary material presented herein demonstrating the cell adhesive properties imparted to a surface treated with disclosed peptides and methods of producing and using such treated surfaces. The treated surfaces are suitable for the culture of species and type of cell including, for example, porcine, murine, insect and human cells. Applicants have used a variety of cells in demonstrating the present invention, including, by way of example and not limitation, human foreskin fibroblast (HFF) cells, porcine aortic endothelial (PAE) cells, embryonic and newborn tissue cells. However, the present invention may be used in conjunction with any species or tissue source of cell, and is not limited to use with any one particular type of cell. The following paragraphs outline the certain preferred methods of culturing particular cell types used to demonstrate the present invention.

Cell Culture Procedures

3T3 CELLS

NIH/3T3 cells, an immortal cell line of embryonic cells established from Swiss mouse embryos, were obtained from the American Type Culture Collection cell repository (ATCC # CRL 1658). Cultures were maintained in Dulbecco's modified Eagle's medium supplemented with 10% fetal calf serum and incubated at 37° C. in a humidified 5% $CO_2$ atmosphere. Confluent monolayers of cells were harvested by incubation in a solution of 0.5% trypsin and 0.53 mM EDTA in phosphate buffered saline (PBS) at 37° C. for 15 minutes. Cells were resuspended in fresh medium and subcultivated by allowing cells to attach and grow to in new culture dishes.

HUMAN FORESKIN FIBROBLASTS

Human foreskin fibroblasts (HFFs) are primary cell lines that are isolated from neonatal foreskin tissue from Seton Hospital, neonatal ward, Austin, Texas. About 5–10 newborn foreskins are collected aseptically in sterile PBS, minced into 5 $mm^2$ pieces, and incubated in trypsin-EDTA for 4 hours. HFFs were collected by centrifugation at 200 g for 5 minutes and resuspended in Dulbecco's modification of Eagle's medium (DMEM, Mediatech) supplemented with 10% fetal calf serum (GIBCO), 400 u/ml penicillin (Irvine) and 400 ug/ml streptomycin (Irvine) and incubated at 37° C. in a humidified 5% $CO_2$ atmosphere. Cells were subcultivated by trypsinizing confluent monolayers, suspending cells in fresh medium, and seeding cells into new flasks. HFFs were maintained in culture for up to 20 passages before they are discarded.

PORCINE AORTIC ENDOTHELIAL CELLS

Porcine endothelial cells were obtained from sacrificed miniature swine. The endothelial cells were isolated by the method of Jaffe, et al. (1973, *J. Clin. Invest.*, 52: 2745–2756). Specifically, porcine aorta tissue segments from sacrificed miniature swine were rinsed with warm (37° C.) PBS to remove blood and placed in 10 cc syringes. The lumen of the segments were then filled with a 100 $\mu l/ml$ solution of Sigma Type II collagenase. The tissue was then incubated for 30 min. at 37° C. The lumen of the aorta was then washed with PBS, and the cells were centrifuged at 200 g for 5 mins. and resuspended in Medium 199 supplemented with 20% fetal calf serum and antibiotic. The suspension was added to culture flasks and the cultures were maintained at 37° C. in a humidified, 5% $CO_2$ atmosphere.

Human Umbilical Vein Endothelial Cells

Human umbilical vein endothelial cells (HUVECs) are primary cell lines that are isolated from postpartum umbilical cords from Seton Hospital, maternity ward, Austin, Tex. by the method of Jaffe et al. (1973, J. Clin. Invest., 52:2745–2756). Postpartum umbilical cords are clamped in 5–12 inch sections, cut from the placental tissue, and collected aseptically in sterile PBS. The clamps are removed from the cut cords, clotted blood in the umbilical vein is extruded out by applying gentle pressure to the cord. Blood is washed from the vein by penetrating one end of the vein with a sterile pipet and gently flowing sterile PBS through the lumen of the vein. The open end of the vein is then clamped externally with a hemostat to seal off the vein and PBS containing 240 U/ml of Type II Collagenase (Sigma) was added through the cannula until the vein was completely filled with the enzyme solution. The cannula was removed and the open end of the vein was clamped so that the cord could be incubated with this solution for 30 minutes at 37° C. The hemostats were removed after the 30 minute incubation period and the enzyme solution containing HUVECs was drained into a sterile centrifugation tube. An additional 20 ml of sterile PBS was run through the lumen of the vein and collected into the sterile centrifuge tube. The HUVECs in this tube collected by centrifugation at 200 g for 5 minutes and resuspended in Medium 199 (M199, GIBCO) supplemented with 20% fetal calf serum (GIBCO), 400 U/ml penicillin, 400 $\mu g/ml$ streptomycin (GIBCO), 100 $\mu g/ml$ endothelial cell growth supplement (Collaborative Research) and 100 $\mu g/ml$ porcine heparin (Sigma) and incubated at 37° C. in a humidified 5% $CO_2$ atmosphere. Cells were subcultivated by trypsinizing confluent monolayers, suspending cells in fresh medium, and seeding cells into new flasks. HUVECs were maintained in culture for up to 5 passages before they are discarded.

Human Vascular Smooth Muscle Cells

Human vascular smooth muscle cells (HVSMCs) are primary cell lines that are isolated from postpartum umbilical cords from Seton Hospital, maternity ward, Austin, Tex. by the method of Jaffe et al. (1973, *J. Clin. Invest.*, 52:2745–2756). Postpartum umbilical cords from which HUVECs were isolated were traumatized by repeatedly crushing the cord externally with a hemostat. PBS containing 240 U/ml of Type II Collagenase (Sigma) was added to the lumen of the vein until the vein was completely filled with the enzyme solution. The cord was clamped so that the cord could be incubated with this solution for 30 minutes at 37° C. The hemostats were removed after the 30 minute incubation period and the enzyme solution containing HVSMCs was drained into a sterile centrifugation tube. An additional 20 ml of sterile PBS was run through the lumen of the vein and collected into the sterile centrifuge tube. The HVSMCs in this tube collected by centrifugation at 200 g for 5 minutes and resuspended in Medium 199 (M199, GIBCO) supplemented with 20% fetal calf serum (GIBCO), 400 U/ml penicillin, 400 μg/ml streptomycin (GIBCO), 100 μg/ml endothelial cell growth supplement (Collaborative Research) and 100 μg/ml porcine heparin (Sigma) and incubated at 37° C. in a humidified 5% $CO_2$ atmosphere. Cells were subcultivated by trypsinizing confluent monolayers, suspending cells in fresh medium, and seeding cells into new flasks. HVSMCs were maintained in culture for up to 5 passages before they are discarded.

Human Blood Platelets (Plt)

Human blood platelets were obtained from heparinized whole blood (4 U/ml) which was centrifuged at 250 g for 15 minutes to obtain platelet rich plasma (PRP). Blood was collected from healthy male nonsmoking donors. PRP was removed from the centrifuged blood and used in platelet spreading assays. Prestimulated platelets (Prestim. Plt) were treated with 5 μM ADP prior to determine platelet spreading.

The following examples are presented to describe preferred embodiments and utilities of the present invention and are not meant to limit the present invention unless specifically indicated otherwise in the claims appended hereto.

Example 1 describes the method by which particularly preferred peptide fragments were synthesized.

Example 2 describes the derivatization of a PHEMA polymer surface.

Example 3 describes the derivatization of a PET polymer surface.

Example 4 describes the preferred method of preparing a primary cell culture from foreskin tissue.

Example 5 describes the adhesion of cells to a derivatized PHEMA and PET polymer surface.

Examples 6, 7 and 8 describe the derivatization of a glass surface, the cell adhesive and supportive characteristics of such a derivatized glass surfaces and the comparative cell supportive characteristics provided by various peptides to a derivatized verses non-derivatized glass surface.

Example 9 describes the relative stability of a derivatized PET polymer and glycophase glass surface to heat and proteolysis.

Example 10 presents a comparative study on the cell supportive characteristics of a pretreated verses a non-pretreated PET polymer surface.

Examples 11 and 12 demonstrate proposed methods of using the described surface derivatization processes with a biomedical implant (Example 11—indwelling catheter; Example 12—nerve growth guide).

Example 13 describes HFF cell adhesion and spreading on treated surfaces with various levels of peptide substitution.

Example 14 describes glycophase glass—a model cell nonadhesive substrate to which peptides can be coupled.

Example 15 describes glycophase glass coupled with RGD materials which support the adhesion of fibroblasts and endothelial cells but not platelets.

Example 16 describes glycophase glass coupled with YIGSR materials which support the adhesion of fibroblasts and endothelial cells but not platelets.

Example 17 describes glycophase glass coupled with PDSGR—materials which support the adhesion of fibroblasts and endothelial cells but not platelets.

Example 18 describes glycophase glass coupled with REDV—materials which support the adhesion of endothelial cells but not fibroblasts or platelets.

Example 19 describes glycophase glass coupled with IKVAV materials which do not support HLFVEC or platelet spreading, but should support neurite outgrowth.

Example 20 describes polyethylene terephthalate to which polyethylene glycol has been immobilized—a polymeric cell-nonadhesive substrate to which peptides can be attached (abbreviated PET/PEG).

Example 21 describes PET/PEG coupled with RGD-materials which support the adhesion of fibroblasts and endothelial cells but not platelets or vascular smooth muscle cells.

Example 22 describes PET/PEG coupled with REDV-materials which support the adhesion of endothelial cells but not fibroblasts or platelets or vascular smooth muscle cells.

Example 23 describes PET/PEG coupled with IKVAV-materials which do not support HUVEC or platelet spreading, but supports HFF spreading and should support neurite outgrowth.

Example 24 describes a solution technique to incorporate polyethylene oxide and other water soluble polymers into surfaces of polymeric biomaterials.

EXAMPLE 1—SMALL PEPTIDES

This example demonstrates particularly preferred methods of synthesizing peptides having less than 12 amino acid residues and including at least the amino acid sequence arginine-glycine-aspartic acid (RGD). This sequence is a particular minimal cell attachment sequence recognizable by cells in cell-receptor mediated cell adhesion.

The peptides used in these studies, including GPDSGRY, GIKVAVY, GREDVY, GRGD, GRGE, GYIGSR, GRGDY, GRGEY, and GYIGSRY, were synthesized by known procedure at the University of Texas Southwestern Medical School peptide synthesis laboratory or obtained from Biosynthesis, Inc., Denton Tex.

EXAMPLE 2—PREPARATION OF PHEMA POLYMER SURFACE

This experiment was designed to describe one particularly preferred method of preparing a polymer surface with small peptide fragments covalently attached thereto. PHEMA (poly(hydroxyethyl methacrylate)), is a hydrogel which has been found unable to support cell adhesion in its untreated state.

The particularly preferred peptides GRGD and GYIGSR were grafted to the polymer surface using the PHEMA surface hydroxyl groups and the terminal primary amine of the glycine linker arm of the peptide using tresyl chloride activation. The G group at the terminal end of each respective peptide was used to add distance between the surface-active peptide (GRGD) and the polymer surface.

More particularly, the coupling method utilized activation of PHEMA surface hydroxyl moieties by tresyl chloride in an organic solvent for the reaction components but a nonsolvent for the polymer. PHEMA films did not require pretreatment, since their surfaces are amply supplied with hydroxyethyl groups. The cell adhesive promoting activities of this modified surface were determined as outlined in Example 4, where in vitro cell adhesion and spreading assays were performed. The tresyl leaving group was then displaced in an aqueous solvent by the terminal amine of the peptide GRGD or GYIGSR.

The unmodified PHEMA films were then tresyl activated in 20 ml dry ether containing 20 $\mu$l of 2,2,2-trifluoroethanesulfonyl chloride (tresyl chloride) and 2 ml of triethylamine for 15 minutes at room temperature. Activated films were then rinsed with 0.2M sodium bicarbonate pH 10 buffer and placed in the same buffer containing 80 ng/ml GRGD for 20 hours at room temperature to couple the peptide.

EXAMPLE 3—PREPARATION OF POLY(ETHYLENE TEREPHTHALATE) (PET) POLYMER SURFACE

This experiment was designed to describe one particularly preferred method of preparing a surface devoid of hydroxyl moieties so as to facilitate the inclusion of small peptides thereto to promote cell adhesion.

The PET surface is a polymer which is devoid of hydroxyl moieties, and therefore the surface must be pretreated before the surface is thereafter modified with a peptide. Specifically, the PET film surface was modified via an electrophilic aromatic substitution which added hydroxymethyl groups to the surface. The reaction was carried out at room temperature and atmospheric pressure. The films were then immersed in 18.5% (v/v) formaldehyde and 1M acetic acid for about 4 hours. The pretreated PET surface was then modified exactly as described for the PHEMA surface as outlined in Example 2.

The following listing presents the most preferred method of pretreating a polymer surface, such as a PET matrix, which does not include hydroxyl moieties. The surface modification of hydroxyl moieties and attachment of peptides fragments thereto was accomplished with the following protocol:

1. Addition of surface hydroxymethyl moieties—to the PET polymer surface by performing an electrophilic aromatic substitution of surface groups or the polymer surface, wherein the PET polymer is immersed in 18.5% (v/v) formaldehyde and 1M acetic acid for 4 hours at room temperature.

2. Tresyl Activation—of surface hydroxyl moieties wherein the pretreated PET film is immersed in 20 ml. dry ether containing 40 $\mu$l of 2,2,2-trifluoroethanesulfonyl chloride (tresyl chloride) and 2 ml. of triethylamine for 15 minutes at room temperature.

3. Rinse—activated PET film was then rinsed with 0.2M sodium bicarbonate pH 10 buffer at room temperature to couple the peptide.

4. Peptide Coupling to Surface—rinsed PET films were then placed in the same buffer containing 80 ng/ml GRGD or GYIGSR peptide for 20 hours.

EXAMPLE 4—PRIMARY CELL CULTURE FROM HUMAN FORESKIN TISSUE

Human foreskin fibroblasts (HFFs) are primary cell lines that were isolated from neonatal foreskin tissue from Seton Hospital, Neonatal Ward, Austin, Tex. The following procedure was used to establish primary cell lines from these tissues: 5–10 foreskins were collected aseptically in sterile PBS, minced into 5 mm$^2$ pieces, and incubated in trypsin-EDTA for 4 hours. HFFs were collected by centrifugation at 200 g for 5 minutes and resuspended in Dulbecco's modification of Eagle's medium supplemented with 10% fetal calf serum. Cells were subcultivated by trypsinizing confluent monolayers, suspending cells in fresh medium, and seeding cells into new flasks. HFFs were maintained in culture for up to 20 passages before they were discarded.

EXAMPLE 5—CELL ADHESION STUDIES ON DERIVATIZED PHEMA AND PET POLYMER SURFACES

This experiment was designed to determine if a polymer surface could be designed and synthesized which would support receptor-mediated cell adhesion in the absence of any intermediate adsorbed proteins, i.e., to produce a surface that was entirely self-sufficient in its support of cell adhesion and spreading. Immobilization of entire proteins, such as collagen or fibronectin, can accomplish this but is associated with the difficulties of proteolysis, protein degradation, and protein denaturation. To circumvent this, the small, thermally stable peptide region of most CAMs, Arg-Gly-Asp (RGD) was covalently coupled to the surface of polymer films with a Gly N-terminal linker in the form of Gly-Arg-Gly-Asp (GRGD). This produced stable surfaces that were intrinsically bioadhesive, i.e., the material surfaces contained groups with a high affinity for cell-surface receptors completely independent of adsorbed CAMs from the culture medium. This surface modification provided a systematic methodology for developing well characterized substrata which simplifies optimization of a culture system. Mouse NIH-3T3 (ATCC # CRL 1658) fibroblasts were washed and inoculated in serum-free medium on both treated and untreated PHEMA substrata. Treated PHEMA substrata was prepared as outlined in Example 2.

CULTURE METHODS

NIH/3T3 fibroblasts (ATCC # CRL 1658, Rockville Md.) were cultured in DMEM supplemented with 10% calf serum in a humidified 5% carbon dioxide atmosphere at 37° C. Porcine aortas were obtained from sacrificed miniature swine. Endothelial cells were isolated by the method of Jaffe, et al. (1973, *J. Clin. Invest.*, 52: 2745-2756) with a modification to facilitate profusion of the lumenal surface of the vessel with collagenase. Porcine aortic endothelial cells (PAE) were maintained in DMEM supplemented with 10% fetal calf serum with the same incubation conditions as above.

SURFACE MODIFICATION PROCEDURE

GRGD was grafted on polymer surfaces via the glycyl terminal amine using the tresyl chloride immobilization method of Nilsson and Mosbach and as described in Examples 3 and 4. Two polymer surfaces were modified, poly(hydroxyethyl methacrylate) (abbreviated PHEMA) and poly(ethylene terephthalate) (abbreviated PET). The coupling method utilized activation of surface hydroxyl moieties by tresyl chloride in an organic solvent for the reaction components, which is also a nonsolvent for the polymer. The tresyl leaving group was then displaced in aqueous solvent by the terminal amine of the peptide.

Poly(ethylene terephthalate) (PET) has no available hydroxyl groups for tresyl chloride activation, therefore a surface hydroxylation procedure was developed. An electrophilic aromatic substitution which adds hydroxymethyl groups to the PET films was employed (FIG. 1). Specifically, the commercially available PET films were immersed in 18.5% (v/v) formaldehyde and 1M acetic acid for four hours at room temperature, as particularly defined in Example 3. PHEMA films did not require pretreatment since their surfaces are amply supplied with hydroxyethyl groups.

The modified PET and unmodified PHEMA films were tresyl activated in 20 ml dry ether containing 40 $\mu$l of 2,2,2-trifluoroethanesulfonyl chloride (tresyl chloride) and 2 ml of triethylamine for 15 minutes at room temperature. Activated films were then rinsed with 0.2M sodium bicarbonate pH 10 buffer and placed in the same buffer containing about 80 ng/ml GRGD for 20 hours at room temperature to couple the peptide. FIG. 2 graphically depicts a modified PET film with hydroxymethyl moieties and the subsequent steps involved with tresyl activation and GRGD coupling.

CELL SPREADING ASSAY

Figure 3B:

NIH/3T3 and PAE cells were detached from culture flasks by trypsinization and suspended in serum-free medium (DMEM with 1 mg/ml bovine serum albumin (BSA)). The cells were washed twice by centrifugation in the BSA containing medium and seeded at a density of 3,000 cells per cm$^2$ of film, unless otherwise noted, in serum-free medium and incubated in the normal culture environment. Spread cells were scored by morphological features such as distinct nuclei, pseudopodia, and polygonal shape (FIGS. 3A and 3B). Cells were visualized at 200X magnification using Hoffman modulation contrast optics on a Leitz Fluovert inverted stage microscope. Cell growth was also assessed by determining spread cell counts at various time points, for cells cultured in media supplemented with 10% calf serum.

ACTIN STRESS FIBER VISUALIZATION

NBD Phallacidin (7-nitrobenz-2-oxa-1,3-diazolyl-phallacidin) (Molecular Probes, Inc. Eugene, Oreg.) was employed to visualize actin stress fibers and microfilament bundles in cells attached to the modified surfaces. Samples were prepared according to the manufacturer's procedure and 1000X images were viewed utilizing the Fluovert microscope equipped with a Leitz E3 excitation filter and UV illumination.

SOLUBLE PEPTIDE COMPETITION STUDIES

In the competition studies, 3T3 fibroblasts were preincubated for 30 minutes in either serum-free medium containing about 90 ug/ml RGDS or no peptide. The cells were then inoculated at a density of about 3000 cells/cm$^2$ on GRGD derivatized PET and spreading was determined after three hours incubation under normal culture conditions.

Figure 4:
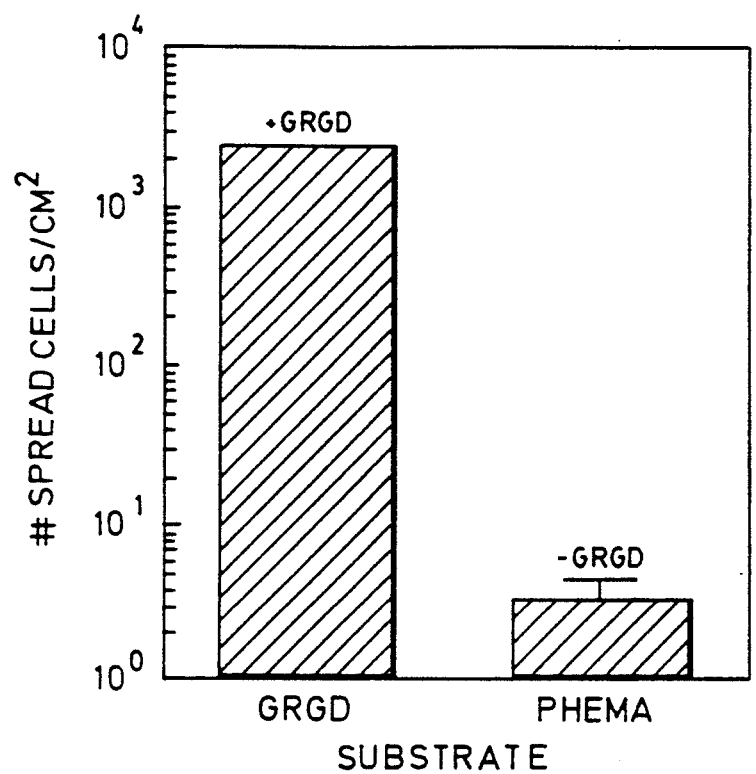
FIG. 4 shows the spreading of 3T3 fibroblasts on GRGD coupled and untreated PHEMA films in a serum-free culture medium. Extent of cell spreading was determined 3 hours after seeding of the substrates.

The GRGD derivatized substrates were characterized by their ability to support active adhesion of cells on their surfaces. The PET pretreatment was optimized by coupling GRGD to tresyl chloride activated films that were hydroxylated for various time periods. Cell spreading assays using NIH/3T3 fibroblasts were performed to determine conditions that supported a maximal response. Four hours pretreatment appeared to be optimal for maximum cell adhesion and spreading. PHEMA films were derivatized with GRGD utilizing low concentrations of peptide (80 ng/ml) which resulted in an increase in cellular adhesion by three orders of magnitude (FIG. 4).

Figure 5:
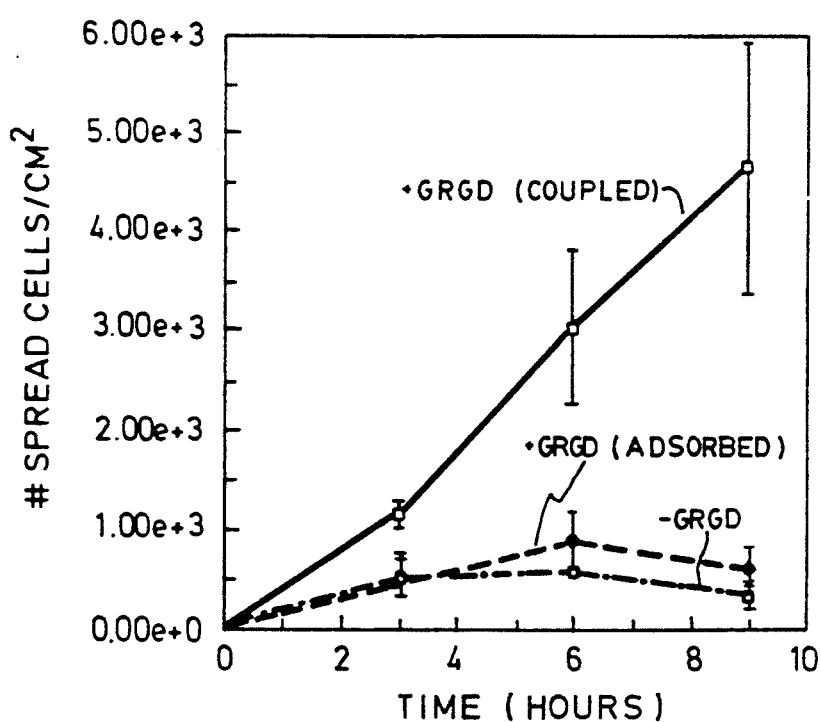
FIG. 5 shows a comparison of 3T3 spreading on GRGD coupled PET (solid curve, open boxes) versus GRGD adsorbed to PET (hatched curve, solid diamonds) and untreated PET (dot-hatched curve, open boxes).
Figure 6:
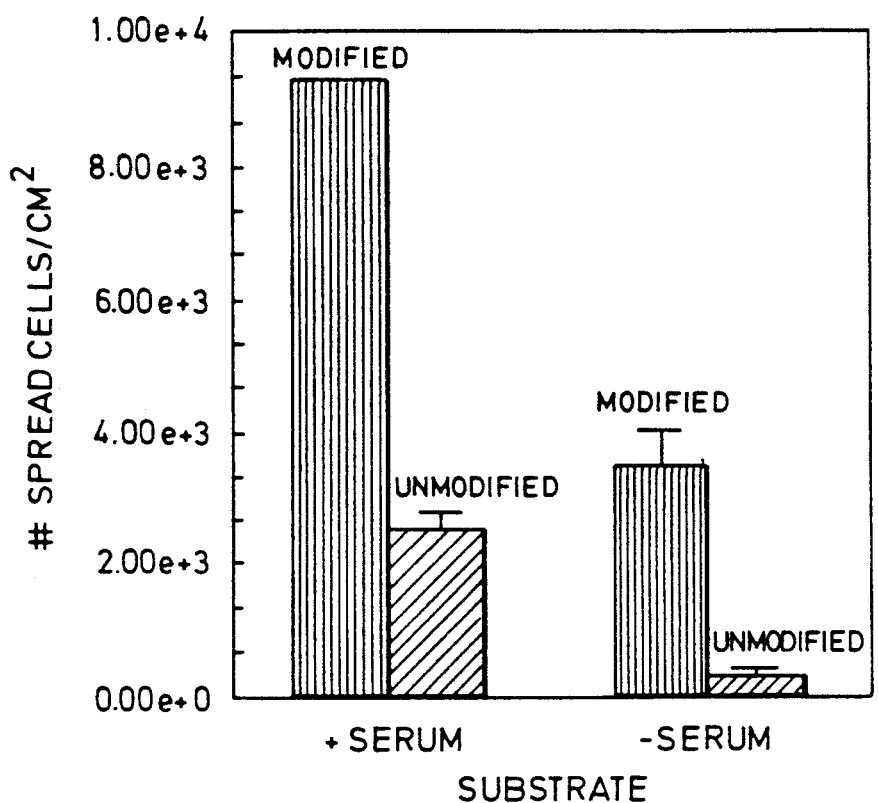
FIG. 6 shows the amount of 3T3 spreading on the modified (solid bars) and unmodified (hatched bars) films in a serum-free and complete medium. The extent of cell spreading was determined 2 hours after inoculation on each film. Cells were seeded at a density of 10,000 cells/cm$^2$.

Comparison of GRGD coupled PET films with pretreated untresylated films that were incubated with GRGD for the normal coupling time demonstrated that either little peptide adsorbed to the latter films or that the adsorbed peptide was not available for the receptor-mediated adhesion response (FIG. 5). The GRGD modified surfaces supported much better 3T3 cell adhesion than the untreated PET even in the presence of serum, which is indicative of an intrinsic activity on the modified surface (FIG. 6).

Figure 7:
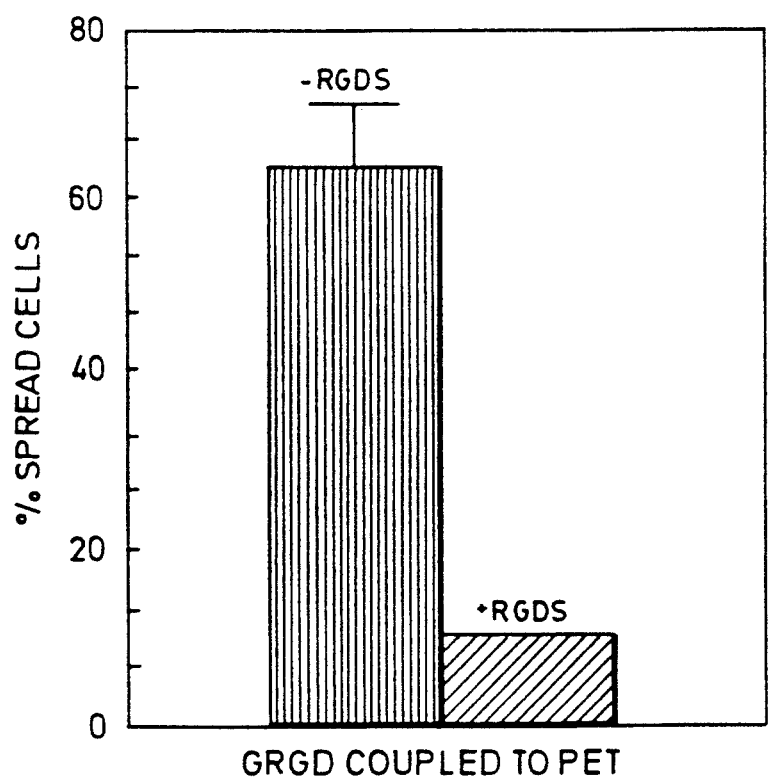
FIG. 7 shows the effects of soluble RGDS on spreading of 3T3 cells on the GRGD derivatized PET films in serum-free culture medium. Cells were preincubated for 30 minutes with RGDS prior to inoculation of the films. The extent of cell attachment was determined 3 hours after inoculation. Cells preincubated with RGDS (hatched bar). Untreated control cells (solid bar).

The competition experiment resulted in a 75% reduction of attachment to the modified surfaces in the presence of about 90 ug/ml RGDS, which further demonstrates the biospecific activity of the substrates (FIG. 7). Gross morphology (FIGS. 3A and 3B) of spread 3T3 fibroblasts in serum-free medium on the modified films appeared normal (FIGS. 3A and 3B).

That no cytoskeletal organization is observed on RGDS modified surfaces indicates that the complete adhesive response of this cell line and others is not obtained on RGDS modified surfaces. This is not a general phenomenon however, as some cell types including normal rat kidney fibroblasts and Nil 8, a normal hamster fibroblast cell line, have been shown to fully respond to substrates containing only RGD peptides (14). Growth on the GRGD derivatized-PET was serum dependent and was similar to that on unmodified PET (FIG. 8), but the initial attachment and spreading was more rapid, as indicated by the observation that the GRGD curve leads (open boxes) the control curve (solid diamonds) in this figure.

Attachment and spreading of porcine aortic endothelial cells on the GRGD coupled surfaces was also serum independent as expected, since vascular endothelial RGD directed receptors have been characterized (15). PAE cell spreading in complete medium was much more extensive on the GRGD derivatized films than the untreated films at four hours, but both surfaces had confluent monolayers of cells at twenty four hours. These observations indicate that the kinetics of PAE cell attachment was more rapid on the modified surface.

Applicants' disclosed methods provide a means for obtaining stable, chemically defined surfaces for use in studying cellular responses to insoluble extracellular matrix signals. It provides a means by which to decouple cell adhesion and spreading from protein adsorption. In this sense, it may be useful for those who prefer to use serum-free cell culture media (i.e., media in which purified proteins are added individually rather than introduced from serum) in that cell adhesion molecules (CAMs) do not need to be included. Whether these surfaces are capable of supporting cell growth at very low serum concentrations remains to be determined.

It should be understood that, in the presence of the media proteins, the GRGD surface is rapidly covered by adsorbed proteins. This is not problematic, however, as Applicants' studies with albumin in the culture media (FIGS. 4, 5, 7) indicated that the high affinity RGD-integrin association is capable of competing favorably with the adsorbed proteins. Cell detachment may be accomplished by calcium chelation, as the RGD-integrin affinity is calcium dependent.

It should also be noted that cell function is highly dependent upon the cell attachment surface (16, 17). This surface may provide a local environment that is closer to the one in vivo, and hence stimulate stronger adhesion and/or higher productivity.

EXAMPLE 6—PEPTIDE DERIVATIZATION OF A GLASS SURFACE

The present example was designed to outline the most preferred method of derivatizing a ceramic surface, such as glass, to provide a cell receptor-mediated adhesion-promoting substrate.

Glycophase glass was prepared by the method of Ohlson et al. (18). Glass coverslips (18 by 18 mm; Thomas) were soaked in 0.5M sodium hydroxide for two hours, rinsed in deionized water, and immersed in an aqueous solution (1% pH 5.5) of (3-glycidoxypropyl)-trimethoxysilane (Petrarch Systems, Inc.). The preparation was heated and maintained at 90° C. for 2 hours. The pH was then adjusted to 3.0 followed by heating again for 1 hour to convert the oxirane moieties on the derivatized glass to glycol groups. Dry glycophase glass coverslips were rinsed with dry acetone (dried over molecular sieve 4A; Fisher). To about 1 ml of dry acetone, about 200 $\mu$l of dry pyridine and about 100 $\mu$l of dry tresyl chloride (Fluka) were added. A minimal volume of this mixture was added to the upper surface of each glycophase glass coverslip placed in a glass crystallization dish. The reaction was allowed to proceed for about 10 minutes at room temperature, then the coverslips were rinsed in about 1 mM hydrochloric acid and finally rinsed in an about 0.2M sodium bicarbonate buffer at pH 9 (coupling buffer). Coupling buffer containing between about 5-30 ng/ml of peptide, preferably about 10 ng/ml, was added at a minimal volume on the coverslips and incubated for about 20 hours at room temperature to graft the peptide to the surface. The peptides used in this study were synthesized as outlined in Example 1. The peptide containing buffer was removed after an about 20 hour incubation period and replaced with coupling buffer containing an about 0.8M beta-mercaptoethanol. The coverslips were incubated for about 2 hours so that unreacted tresyl groups would react with a nonadhesive moiety.

Measurement of Peptide Surface Concentration

GRGDY was radiolabeled by adding about 20 ug of peptide to phosphate buffered saline, pH 7.4, containing about 5.0 mCi of Na$^{125}$I and incubating for 15 about minutes at room temperature with Iodobeads (Pierce) according to the manufacturer's instructions. The labeled peptide was purified by loading the reaction mixture on a Sep-Pak C$_{18}$ sample preparation cartridge (Waters) that was washed with methanol-H$_2$O-trifluoroacetic acid (TFA) (80:19:1 v/v) and reequilibrated with PBS. The cartridge was washed with 1% v/v TFA to eluate unincorporated iodine. The reaction mixture was fractioned using 10% stepwise increases in methanol concentration in 1% TFA with the methanol-H$_2$O-TFA (80:19:1 v/v) as the final eluant. The cartridge was washed with each concentration until the radioactivity returned to a baseline level. Each fraction was analyzed for peptide content by measuring absorbance at 220 nm (epsilon=8441 M$^{-1}$ cm$^{-1}$). Greater than 90% of the eluted peptide was in the methanol-H$_2$O-TFA (40:59:1 v/v) fraction, which was lyophilized and reconstituted in PBS. The specific activity of the peptide was then determined after counting a known amount of labeled peptide in an automatic gamma counter (Isoflex, ICN Micromedic Systems). The average specific activity was 44.0±2.0 mCi/mmol.

To determine peptide surface concentrations, radiolabeled peptide was added to coupling buffer (0.2M sodium bicarbonate, pH 10) at various concentrations, and incubated for 20 hours on tresyl activated glass at room temperature. Input concentrations were defined as the moles of soluble peptide available for reaction per unit area of glass surface. Surface concentrations were defined as the moles of peptide coupled per unit area of glass and were determined by counting washed glass samples in a gamma counter and calculating the values based on the specific activity of the labeled peptide.

The synthetic peptides Gly-Arg-Gly-Asp-Tyr (GRGDY) and Gly-Tyr-Ile-Gly-Ser-Arg-Tyr (GYIGSRY), which contain the ligands for two important classes of cell adhesion receptors, were covalently coupled to the non-adhesive modified glass surface, glycerol propylsilane bounded glass (glycophase glass) by the N-terminal Gly. Glycophase glass contains a covalently bound organic layer that imbibes water and reduces protein adsorption similar to hydrogels without the associated problems of swelling and bulk permeation of aqueous solutions. Since glycophase glass absorbs proteins poorly, it alone is not suitable for supporting cell adhesion, even with serum in the medium. Therefore, GRGDY and GYIGSRY were coupled to glycophase glass using the tresyl chloride immobilization method of Nilsson, et al. (1987), Methods Enzymol., 135:65-78). The Nilsson, et al. article is specifically incorporated herein by reference.

The N-terminal "G" was used as a spacer between the adhesive peptide and the surface, and the C-terminal "Y" was used for radioiodination. Since primary amines serve as nucleophiles that react and covalently bind to tresyl-chloride-activated supports, the peptides employed linked to the glycophase glass exclusively through the primary amine of the N-terminal "G". The surface concentration of peptide was measured by $^{125}$I radiolabeling and was 12.1 picomoles/cm$^2$. This derivatization method produces chemically stable substrates, which may be useful in studying receptor-mediated cell adhesion, as the quantity of peptide available at the surface may be precisely measured and controlled.

EXAMPLE 7—ADHESION AND SPREADING OF CELLS ON A PEPTIDE DERIVATIZED GLASS SURFACE

The present examples was designed to determine the effectiveness of the proposed chemical glass surface treatments in promoting the amount and rate of cell adhesion to a glass surface.

SUBSTRATE PREPARATION

Glycophase glass substrates were prepared by the method described in Example 6. These modified substrates supported the adhesion and spreading of cultured human foreskin fibroblasts (HFFs) independently of adsorbed proteins.

PARAMETERS MEASURED

The biological activity of both grafted GRGDY and GYIGSRY was assessed by measuring the adhesion and spreading of HFF in the presence and absence of serum in the medium. Focal contact formation and cytoskeletal organization were also observed on these substrates.

RESULTS

HFF spreading rates were much slower on grafted YIGSR (GYIGSRY) peptide substrates than on the RGD-containing (GRGDY) peptide surfaces. Cells formed focal contacts or absence on the RGD-derivatized substrates in the presence of serum. Focal contacts formed on the YIGSR-grafted surfaces only when serum was present in the medium and had morphologies distinct from those observed on the RGD-containing surfaces (FIGS. 10A–10D; FIGS. 12A–12D).

Serum influenced microfilament organization and the extent of spreading of adherent cells, although adsorption of adhesion proteins was minimal on all surfaces.

EXAMPLE 8—COMPARATIVE STUDIES OF PEPTIDE FRAGMENTS GRGDY, GYIGSRY AND GRGEY ON A DERIVATIZED GLASS SURFACE

Derivatized glass surfaces were prepared according to the method described in Example 6 employing the GRGDY, GRGEY and GYGSRY peptides. HFF cells were then plated onto each of the prepared surfaces. Spreading and growth rate determinations were then made. Untreated glycophase glass was found to support no cell adhesion, even when cells were incubated on this substrate in serum-supplemented medium, which is indicative of a low protein-binding substrate (Table 1).

Beta-mercaptoethanol-grafted glass was equally non-supportive of cell adhesion and spreading, as indicated in the results of the cell spreading studies (FIGS. 2B, D,; 3B, D). Since beta-mercaptoethanol was employed to react with any remaining tresyl groups on the surface of the glass, a non-adhesive background was established on this surface. Furthermore, grafted GRGEY, which does not intrinsically support receptor-mediated cell adhesion and adsorbs proteins similarly to grafted GRGDY, did not support cell adhesion (Table 1). This result suggests that immobilizing GRGDY on glycophase glass does not significantly enhance protein adsorption on this substrate.

Spreading and Growth Rate Determination

HFF cells were prepared as outlined in Example 4. These cells were harvested for experiments and rinsed twice with $Ca^{2+}$- and $Mg^{2+}$-free phosphate buffered saline (PBS) and then incubated in 0.05% trypsin plus 0.53 mM EDTA in PBS (GIBCO) for 10 minutes. Cells were collected by centrifugation and resuspended in serum-supplemented medium or serum-free medium which consisted of DMEM with 2 mg/ml of heat-inactivated (90° C., 10 min.) albumin (Sigma) and antibiotics.

Cells suspended in complete or serum-free medium were seeded on the substrates at a density of about 10,000 cells/cm$^2$ and allowed to attach and spread at 37° C. in 5% $CO_2$. An inverted microscope (Fluovert, Leitz) equipped with a phase contrast objectives and a high resolution video camera (67M series, Dage-MTI) were used to visualize spreading cells at various time points.

Images were digitized with an image processing system (Series 150, Imaging Technology Inc.) and the areas of individual cells were determined by tracing the perimeter of each cell in the digitized images with a tracing pad (Digi-Pad, GTCC) and computing the area enclosed by each trace with an integration routine. At least 100 cells were analyzed and cumulative histograms were constructed for each time period so that cell spreading rates could be determined.

Cell growth in complete medium on substrates was assayed by visualizing cells with 100× phase contrast microscopy. At various time points, cells were counted in ten fields and the number of cells power unit area of growth surface was calculated based on an averaged cell count per area of field.

In the end point cell spreading assays protein synthesis was inhibited by treating cells with 20 ug/ml of cycloheximide for about 30 minutes prior to inoculating them on substrates. The cells were maintained in medium containing cycloheximide throughout the experiment. Cells that were treated with soluble peptide were preincubated with medium containing peptide for about 30 minutes and were maintained in that medium throughout the experiment. Spread cells were scored in 10 fields according to methods described by Massia et al. (1989) (*Biochem. Engin. VI, Ann.* N.Y. Acad. Sci., Vol. 589, pp. 261–270, 1990). The percentage of spread cells per field was calculated by multiplying the ratio of spread cells to the total number of cells per field by 100.

Morphological Studies

Cells adherent to peptide-grafted 24×50 coverslips (Thomas) were mounted in a culture chamber stage and fitted on the Fluorovent inverted microscope. A NPL Fluotar 100× (Leitz) objective was employed so that transmission phase contrast, and interference reflection (IRM) microscopy could be performed on the same field without changing objectives. Phase contrast and IRM images were acquired from live cells immersed in medium and maintained at 37° C. Illumination for phase contrast was provided by a 100 W halogen lamp and a model 050260 power supply (Leitz) equipped with a heat-reflecting filter. A 100 W mercury arc lamp powered by a HBO 100 model 990023 DC source (Leitz) was used for IRM. Images were acquired with a high resolution video camera (70 series, Dage-MTI) and digitized with the Series 150 image processing system. Digitized images were photographed from a high resolution video monitor (model PVM 1271Q, Sony) using Illford Pan F film.

Fluorescence Microscopy

Cells on peptide-grafted glass coverslips at the end of incubation times were rinsed in PBS and fixed for about 20 minutes with 3.7% (v/v) formaldehyde in PBS. They were then rinsed in PBS and permeabilized by incubation at room temperature for about 1 minute in PBS containing about 0.2% (v/v) TRITON X-100. Cells were then rinsed in PBS and stained for F-actin with a 20 minute incubation at room temperature with about 900 ng/ml rhodamine-conjugated phalloidin (Molecular Probes, Inc.). The coverslips were rinsed thoroughly with PBS and mounted on microscope slides in 50% PBS-50% glycerol. These preparations were viewed and photographed on the Fluovert microscope equipped with a 100X PL Fluotar objective (Leitz).

RESULTS

Determination of GRGDY Surface Concentration

Figure 9:
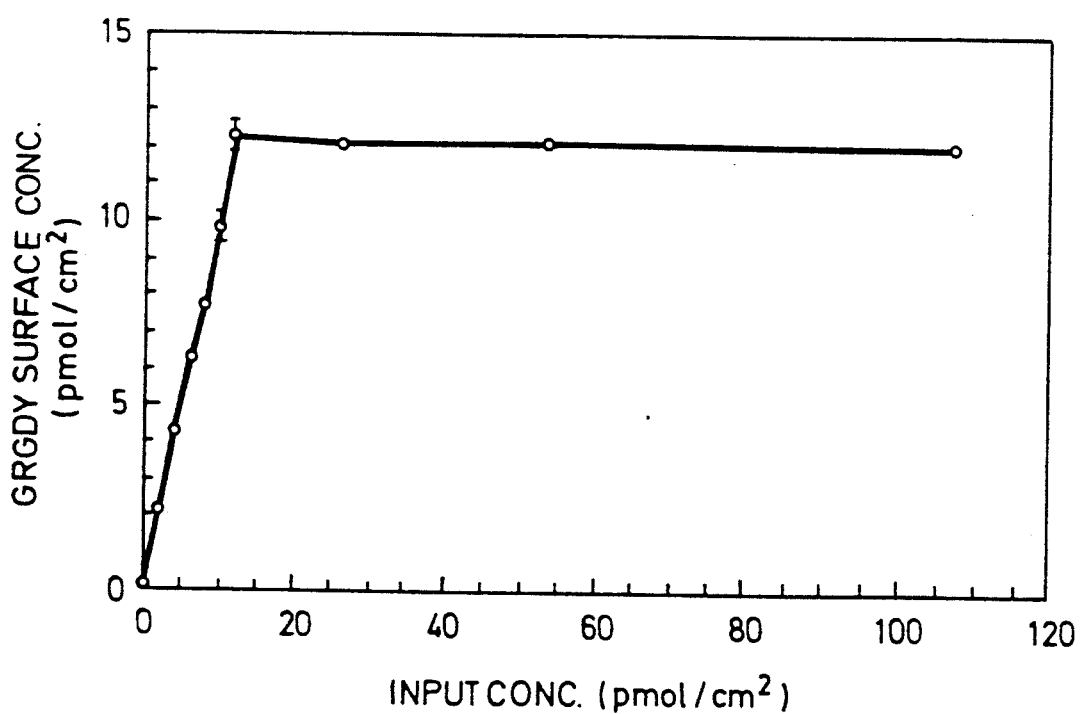
FIG. 9 shows surface concentration of GRGDY-$^{125}$I grafted to glycophase glass was added to coupling buffer (0.2M sodium bicarbonate pH 10) and incubated on tresyl activated glass at room temperature. Input concentrations were soluble peptide available for reaction per unit area of glass surface. Surface concentration is defined as the moles of peptide coupled per unit area of glass and were washed glass samples in a gamma counter and calculating the values based on the labeled peptide. Each point is the average of triplicate determinations surface concentration was 12.1 pmol/cm$^2$.

The number of reactive sites and the corresponding peptide concentration on the surface were determined by titration with the radiolabeled GRGDY (FIG. 9). Surface concentration of grafted GRGDY was determined to increase linearly with increasing concentrations of peptide available for coupling to the surface, reaching a maximum value of 12.1±0.1 picomoles/cm$^2$ (FIG. 9). Subsequent increases in input peptide concentrations above 12.0 picomoles/cm$^2$ did not further increase the surface concentration of the peptide. A maximum surface concentration of 12.1 picomoles/cm$^2$ corresponds to a surface coverage of 73,000 molecules per square micrometer, or a spacing of approximately 3.3 nm between peptides.

HFF Spreading Rates on Peptide-Grafted Substrates

Figure 10A:
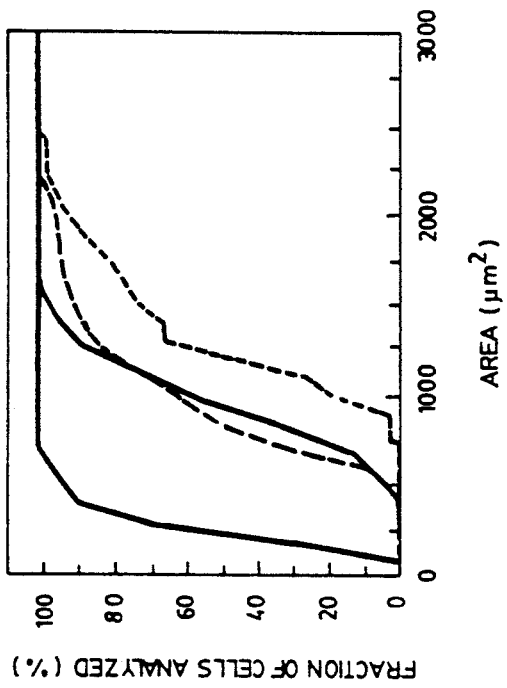
FIGS. 10A–D show cumulative histograms showing the cell areas of HFFs on glycophase glass with GRGDY. Cells were suspended in either complete medium (10A) containing albumin (10C), (10D), and inoculated on the substrates. 10A and 10C represent data collected on the RGD-derivatized glass, whereas (10B) and (10D) represent nonadhesive control surfaces. The areas of individual cells were video microscopy coupled with digital image processing. Cell spreading observed on the peptide-grafted surfaces, even in the absence of serum; there was no cell spreading on the ungrafted surfaces even with serum, and most of these cells were nonadherent. At least 100 cells were analyzed at each time point to generate the cumulative data. Lines: (solid line) 15 minutes; (dotted line) 30 min.; (heavy dashed line) 60 min.; and (light dashed line) 120 min. Midpoint with 50% above and 50% below for the various time points (in order): A: 15 min. 265 $\mu m^2$; 30 min. 906 $\mu m^2$; 60 min., 1113 $\mu m^2$; 120 min., 2130 $\mu m^2$; B: 385,397, 448, 453; C: 248, 950, 864, 1207; D: 377, 325, 388, 388.
Figure 10C:
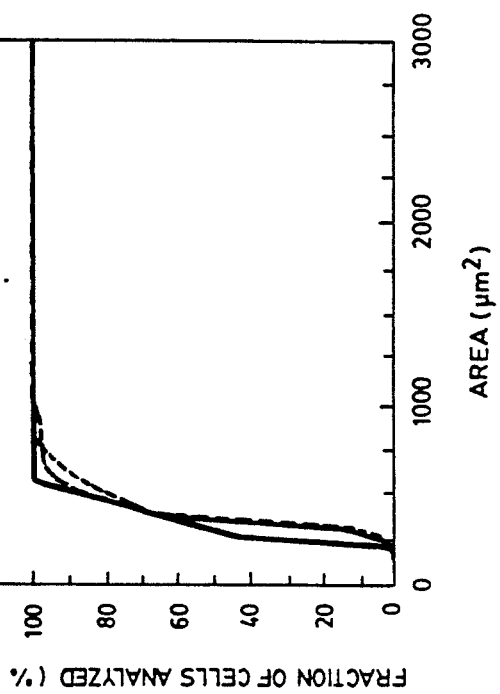
Figure 10B:
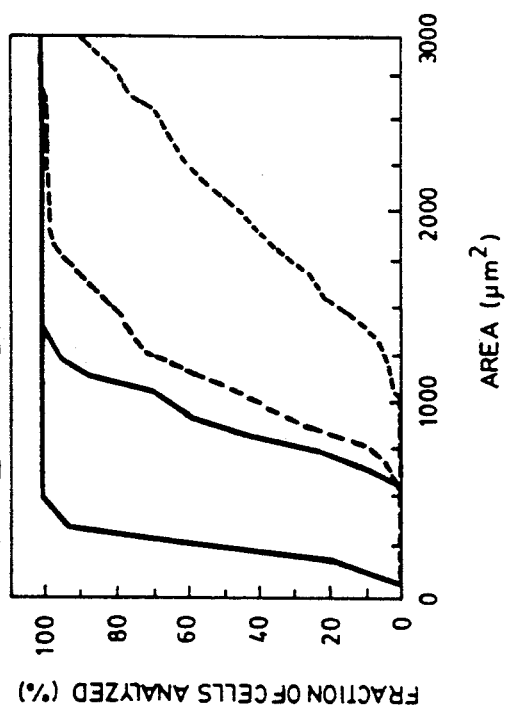
Figure 10D:
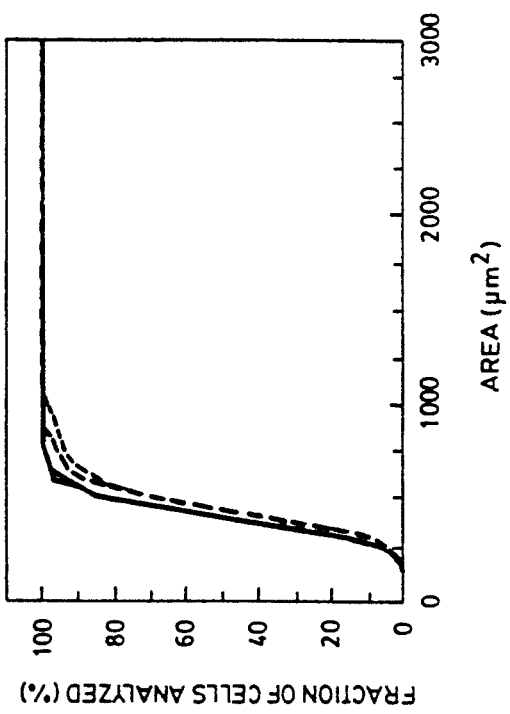

Cells were observed to spread progressively during the 2 hour period on the RGD-derivatized glass, both in the presence and absence of serum, with 50% of the cells analyzed having areas of 2130 μm$^2$ or less 2 hours after seeding in complete medium (FIG. 10A), and 50% of the cells having areas 1210 μm$^2$ or less 2 hours after seeding in serum-free medium (FIG. 10C). The average area of a well-spread cell on tissue culture plastic in complete medium was observed to be 2100 μm$^2$, whereas a non-spread cell had an average area of 355 μm$^2$. The area ranges of cells cultured on the nonadhesive surfaces did not vary over time in the presence or absence of serum, with 50% of the cells having areas less than 500 μm$^2$ (FIGS. 10B, D). These results indicate that no spreading occurred on these surfaces, and most of the cells were observed to be nonadherent.

Cell spreading was also observed on YIGSR-derivatizing glass in the presence and absence of serum. Spreading rates were much slower on grafted YIGSR substrates than on the RGD-containing surfaces, requiring more than 6 hours for complete spreading in complete (FIG. 10A) or serum-free (FIG. 10B) medium. After about 9 hours in serum-free medium, 50% of the cells analyzed had areas 1400 μm$^2$ or less (FIG. 10B), which is comparable to areas of well-spread HFFs on the RGD surfaces in serum-free medium. Serum was observed to enhance cell spreading on the YIGSR surfaces; 50% of the cells analyzed had areas of 2333 μm$^2$ or less (FIG. 10A) 9 hours after inoculation. Nonadhesive control surfaces were identical to the ones prepared for the RGD-derivatized glass studies and cell spreading was not observed on these surfaces; 50% of the cell areas never exceeded 600 μm$^2$ throughout the time frame of the study (FIGS. 10C, D).

Effects of Grafted GRGDY on Cell Growth

Figure 11:
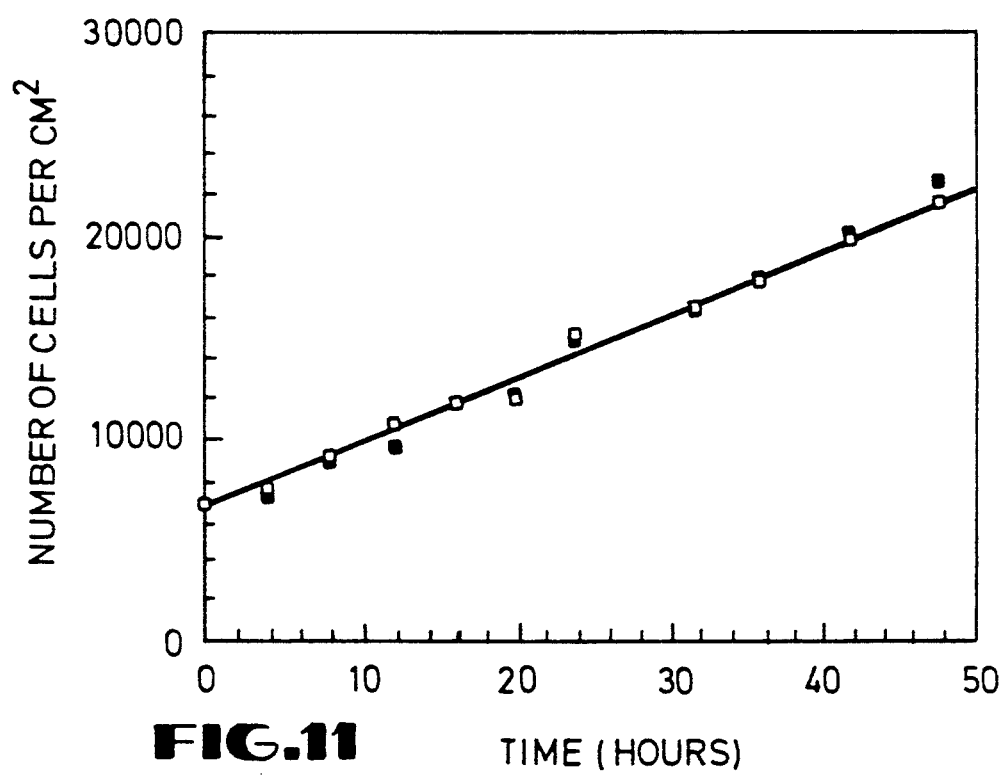
FIG. 11 shows growth of HFFs on GRGDY-derivatized glycophase glass (open squares) and untreated borosilicate glass (solid squares) in DMEM supplemented with 10% fetal calf serum. Cells were visualized with 100× phase contrast microscopy. The number of cells per unit area of growth surface was calculated based on an averaged cell count per area of field from a sample size of 10 fields per time point. The similar growth rates indicate that cells are able to round-up from the peptide-grafted surfaces and to subsequently divide.

The effect of these RGD-containing substrates on cell growth was checked by monitoring growth of HFFs seeded on glass containing coupled GRGDY. No difference in growth rate was observed when we compared growth of cells cultured on RGD-derivatized glass with that of untreated (not glycophase) glass (FIG. 11).

Characterization of Cellular Responses to the Peptide-Grafted Substrates

Since serum enhanced cell spreading on the peptide-containing glass, it was postulated that the peptides grafted to the surface of the nonadhesive glass promoted the adsorption of serum and excreted cellular proteins which would augment cell adhesion and spreading on these substrates. To check this possible effect, the synthetic peptide GRGEY was coupled to glass, and cell spreading on these surfaces was assayed. The substitution of glutamic acid (E) for aspartic acid (D) (an addition of one methylene group to the carboxylic acid side chain) has been demonstrated to abolish the adhesion-promoting activity of the peptide (8) but should have little impact on the way the peptide interacts with potentially adsorbing proteins.

No cell spreading was observed on covalently bound GRGEY after about 8 hours, even when complete medium was used and cellular protein synthesis was not inhibited (Table 1). These findings suggest that the covalently-bound GRGEY and GRGDY peptides do not significantly increase the adsorption of cell adhesion proteins which would promote and enhance cell spreading. This is to say that, the cell adhesive behavior of the peptide grafted surfaces was due to the peptide's affinity for cell-surface receptors and not due to enhanced serum protein adsorption by the peptide.

To determine if protein synthesis played a role in cell spreading on the RGD and YIGSR-linked substrates, and if serum significantly increased the fraction of cells that spread at a time point where spreading was complete, the percentage of spread cells was determined on each surface under different conditions after an 8 hour incubation period. It was observed that neither protein synthesis nor the presence of serum in the medium affected the fraction of cells spread on the RGD-and YIGSR-derivatized glass (Table 1). Cell spreading on both the peptide-grafted surfaces was completely inhibited, however by the presence of soluble peptide in the medium (Table 1), indicating that cellular adhesion on these substrates is governed primarily by cell receptor-ligand interactions.

TABLE 1

| Peptide grafted to surface | Serum in medium (10% v/v) | Cycloheximide in medium (20 ug/ml) | Peptide in medium (200 ug/ml) | Spread cells (%) |
|---|---|---|---|---|
| GRGEY | + | + | − | 0 |
| | + | − | − | 0 |
| | − | + | − | 0 |
| | − | − | − | 0 |
| GRGDY | + | − | − | 87 ± 8 |
| | + | + | − | 80 ± 9 |
| | − | − | − | 91 ± 4 |
| | − | + | − | 83 ± 10 |
| | − | − | +(RGDS) | 0 |
| | − | + | +(RGDS) | 0 |
| GYIGSRY | + | − | − | 78 ± 7 |
| | + | + | − | 82 ± 2 |
| | − | − | − | 81 ± 12 |
| | − | + | − | 90 ± 2 |
| | − | − | +(YIGSRY) | 0 |
| | − | + | +(YIGSRY) | 0 |

Cell-Substrate Contacts and Cytoskeletal Organization

Cells were examined live by IRM and phase contrast microscopy at about 4 hours after seeding on RGD-derivatized substrates and about 8 hours after seeding on YIGSR-derivatized substrates. Fixed specimens were stained with rhodamine-conjugated phalloidin to evaluate microfilament distribution in spread cells. All images were digitized and a high pass filter was employed to enhance detail.

Figure 13A:
FIGS. 13A-D shows phase contrast (13 A, C) and IRM (13 B, D) micrographs of spread HFFs on RGD-grafted glass. Cells were incubated for 4 hours in serum-free (13A, B) or complete medium (13 C, D). Scale bar=10 $\mu m$.
Figure 13B:
Figure 13C:
Figure 13D:
Figure 14A:
FIGS. 14A-D shows phase contrast (14 A, C) and IRM (14 B, D) micrographs of spread HFFs on YIGSR-grafted glass. Cells were incubated for 8 hours in serum-free (14 A, B) or complete medium (14 C, D). Scale bar=10 $\mu m$.
Figure 14B:
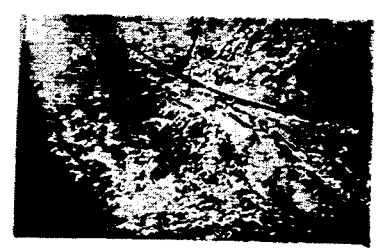
Figure 14C:
Figure 14D:

Cells seeded in the absence of serum on RGD-grafted glass, formed small, round focal contacts that were observed mainly on the outer margins of cells (FIG. 13B). Serum supplemented medium supported formation of large elongated focal contacts typical of cells that spread on cell adhesion molecule-coated substrates (FIG. 13D). Cells spreading on YIGSR-grafted glass did not form focal contacts in the absence of serum (FIG. 14B). Focal contacts were well-defined on this substrate when medium was supplemented with serum (FIG. 14D), however they were morphologically distinct from those of FIG. 13D on the RGD-derivatized substrates. Focal contacts on the YIGSR-derivatized substrates were elongated, similar to those in FIG. 13D, but were predominantly located in the outer margins of cells. Phase contrast images (FIGS. 13A, C; 14A, C) did not reveal any obvious morphological differences between spread cells on the various substrates, but serve as a corresponding image for the IRM images.

Figure 15A:
FIGS. 15A-D shows fluorescent micrographs of HFFs stained for F-actin. HFFs were incubated for 4 hours on RGD-derivatized substrates in serum-free (15 A) and complete (15 B) medium. 15 C and 15 D are spread cells on YIGSR-derivatized substrated after an 8 hour incubation in serum-free (15C) and complete (15D) medium. Scale bar=10 $\mu m$.
Figure 15B:
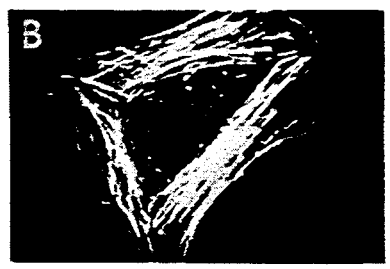
Figure 15C:
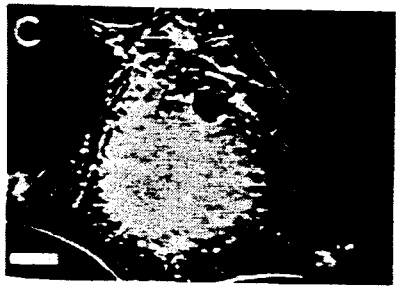
Figure 15D:

Rhodamine-phalloidin staining revealed an extensive network of acting microfilament bundles in spread cells on RGD-grafted glass, that were incubated in serum-free (FIG. 15A) or complete (FIG. 15B) medium. Bundles formed by spreading cells incubated in serum supplemented medium stained more intensely than those formed by cells incubated in serum-free medium, which indicates that thicker fibers formed when serum was present. Cells incubated in serum-free medium on the YIGSR-grafted substrates formed very few microfilament bundles (FIG. 15C), however thick bundles formed when serum was present in the medium (FIG. 15D).

These studies show that adhesion-promoting synthetic peptides of minimal sequences can be covalently grafted to the surface of a nonpermeable, nonadhesive material such as glycophase glass to produce biologically active, chemically well-defined surfaces that support cell adhesion. These substrates may be useful in the study of cell adhesion, as the amount of peptide available on the surface may be precisely measured (FIG. 9) and it is possible to control the amount of peptide grafted competitively by adding controlled amounts of a nonadhesive species, such as glycine, in the coupling buffer. This could be an important requirement for model substrates of receptor-mediated cell adhesion, since it has been recently shown that integrin-mediated cell adhesion to adsorbed RGD-albumin conjugates is very sensitive to the density of RGD-containing groups that are covalently attached to the native protein.

EXAMPLE 9—STABILITY OF PEPTIDE-GRAFTED SUBSTRATES

Radiolabeled GRGDY peptides were covalently grafted to glycophase glass substrates in order to determine how stable the immobilized peptides were to heat and proteolysis. The percent (%) less in radioactivity was interpreted to indicate the percent (%) of immobilized peptide that was degraded and thus unavailable for enhancing cell adhesion.

The data suggests that these peptide-grafted substrates are quite stable to autoclaving (steam sterilization at 121° C.), since no loss of radioactivity was evident after this treatment (Table 2). Also, no radioactivity was lost after culturing cells on these substrates for 1 week. The data also indicates that the treated substrates are stable to cellular proteases.

TABLE 2

| Stability of RGD-derivatized Glycophase Glass | |
|---|---|
| Environmental Stress to the Substrate | % loss of radioactivity |
| Autoclave (121° C., 15 min) | 0 ± 0 |
| Cell Culture (1 week) | 2 ± 1 |
| Exposure to Trypsin | 5 ± 4 |

EXAMPLE 10—PEPTIDE ADSORPTION COMPARISON OF GRGD COUPLED PET SUBSTRATES WITH PRETREATED UNTRESYLATED PET SUBSTRATES

Figure 17:
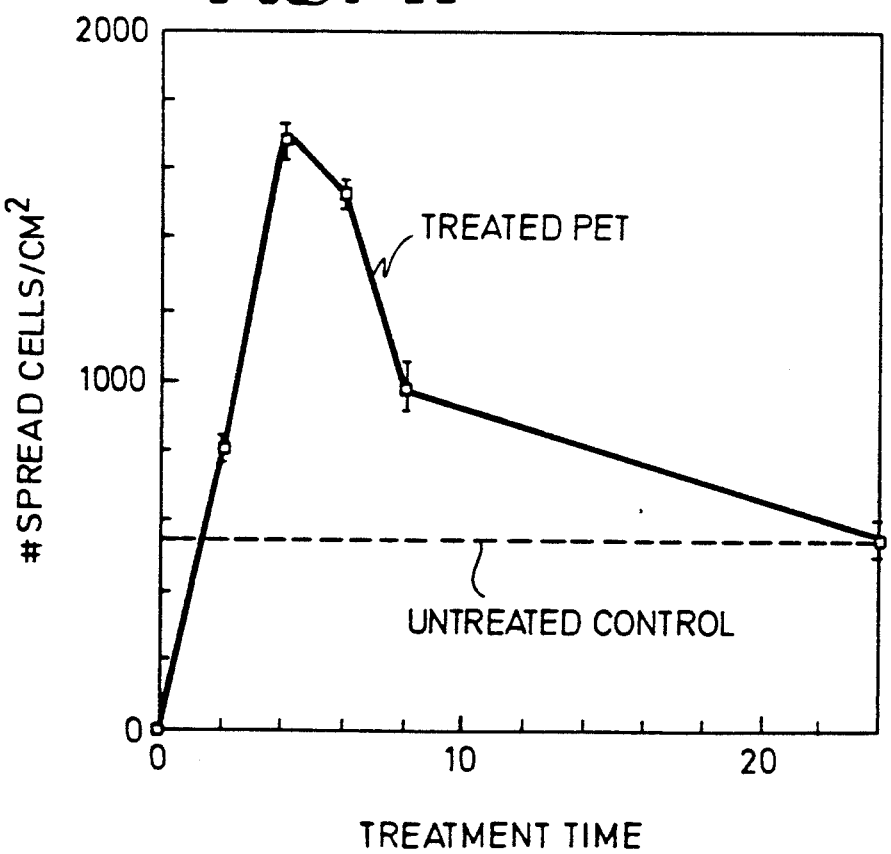
FIG. 17 shows the rate of cell spreading observed on peptide derivatized PET (polymer) surfaces versus nontreated PET (polymer) surfaces.

The GRGD derivatized PET substrates were characterized by their ability to support active adhesion of cells on their surfaces. The PET pretreatment was optimized by coupling GRGD to tresyl chloride activated films that were hydroxylated for various time periods. Cell spreading assays using NIH/3T3 fibroblasts were performed to determine conditions that supported a maximal response. An about four hour pretreatment appeared to be optimal for maximum cell adhesion and spreading (FIG. 17).

Comparison of GRGD coupled PET films with pretreated untresylated films that were incubated with GRGD for the "normal" coupling time (about 20 hours) demonstrated that either little peptide adsorbed to the film or that the adsorbed peptide was not available for the receptor mediated adhesion response (FIG. 5). The GRGD modified surfaces supported much better 3T3 cell adhesion than the untreated PET, even in the presence of serum, which is indicative of an intrinsic activity on the modified surface (FIG. 6). The competition experiment resulted in a 75% reduction of attachment to the modified surfaces in the presence of about 90 ug/ml RGDS, which further demonstrates the biospecific activity of the substrates (FIG. 7).

Figure 8:
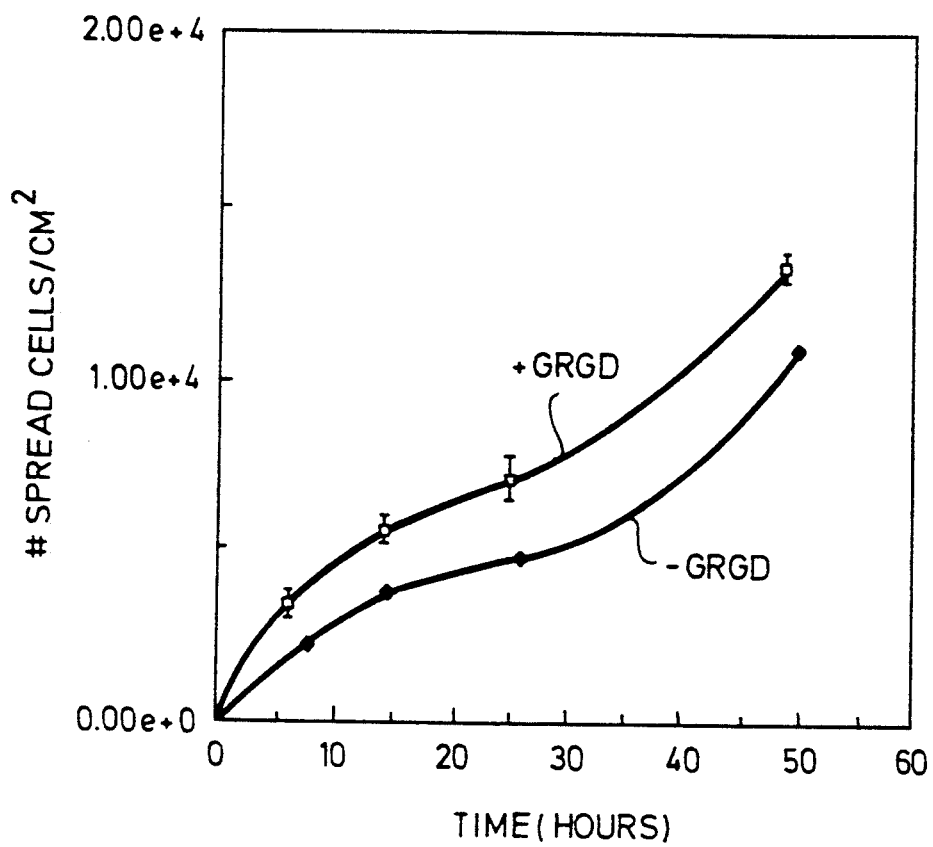
FIG. 8 shows the growth kinetics of 3T3 cells on GRGD derivatized (open squares) and untreated (solid diamonds) PET surfaces. These studies were performed in complete medium.

Gross morphology (FIGS. 3A and 3B) of spread 3T3 fibroblasts in serum-free medium on the modified films appeared normal, however, microfilament bundle and stress fiber formation could not be detected under these conditions. These results indicate, as others have shown with absorbed RGD peptides (19, 20, 14), that the complete adhesive response of this cell line and others is not obtained on these modified surfaces. This is not a general phenomenon however, as some cell types including normal rat kidney fibroblasts and Nil 8, a normal hamster fibroblast cell line, have been shown to fully respond to substrates containing only RGD peptides (14). Growth on the GRGD derivatized PET was serum dependent and was similar to that on unmodified PET (FIG. 8), but the initial attachment and spreading was more rapid, as indicated by the observation that the GRGD curve leads the control curve (FIG. 8).

Figure 16:
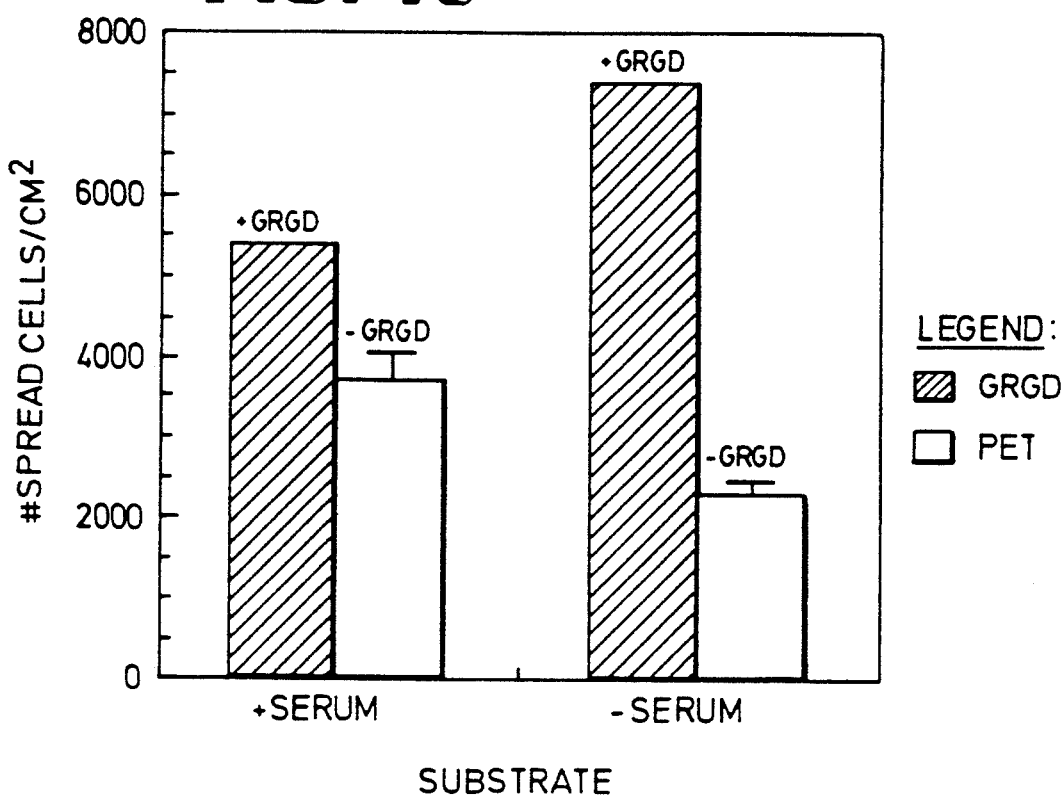
FIG. 16 shows the effect of the absence or presence of serum on porcine aortic endothelial cell spreading in cell cultures established on either PET or GRGD peptide derivatized PET surfaces.

Attachment and spreading of porcine aortic endothelial cells on the GRGD coupled surfaces was also serum independent (FIG. 16). As expected, since vascular endothelial RGD directed receptors have been characterized (15). PAE cell spreading in complete medium was much more extensive on the GRGD derivatized films than the untreated films at four hours, but both surfaces had confluent monolayers of cells at twenty-four hours. These observations indicate that the kinetics of PAE cell attachment was more rapid on the modified surface.

EXAMPLE 11—AN INDWELLING CATHETER WITH A BIOADHESIVE DACRON VELOUR CUFF IN A RABBIT (PROPHETIC)

A dacron velour cuff with an inner diameter of about 1 mm and an outer diameter of about 3 mm would be placed around a polyethylene catheter at the base and glued in place with surgical-grade cement. Prior to placement a cuff would be treated in the acetic acid/formaldehyde solution as described in Example 3 to hydroxylate the surface. The tetrapeptide GRGD would then be covalently attached to the cuff material surface as described in Example 3 by tresyl activation and coupling. The fur of the animal would be shaved along the abdomen, and the skin opened with a lateral cut of about 1 cm length. The catheter would be inserted into a vein, e.g. the descending vena cava, and the cuff would be placed just beneath the skin. The skin would be sutured together around the protruding catheter, such that it covered the cuff. The rates of bacterial infection on the catheter would then be measured. Several of the cuffs would be removed after a period of time, for example, 1, 2, 3 and 4 weeks for histological examination of tissue integration, regrowth, and inflammation. Control experiments would utilize unmodified dacron cuffs.

EXAMPLE 12—A NERVE REGROWTH GUIDE (PROPHETIC)

A polymer tube with a high permeability to water and oxygen with an inner diameter of about 1.5 mm and an outer diameter of about 3 mm would be used as a nerve regrowth guide in the rat. An example of a useful material would be poly(hydroxylethyl methacrylate). The lumen of the tube would be activated and coupled with the peptide GRGD or GYIGSR as described in Example 3. A nerve bundle in one leg would be severed and a section approximately 1 cm long would be removed. Both ends of the nerve bundles would be inserted into the ends of the tubular regrowth guide, and the edges of the guide would be tightly sutured to the epiaxonal tissue. The wound would be closed, and reinnervation would be measured electrophysiologically weekly. Control experiments would utilize unmodified poly(hydroxyethyl methacrylate) tubes.

The following references are cited throughout the Specification, and are hereby specifically incorporated in pertinent part by reference herein.

EXAMPLE 13—COMPARATIVE STUDIES OF GRGDY GRAFTED AT DIFFERENT DENSITIES ON A DERIVATIZED GLASS SURFACE

Figure 18:
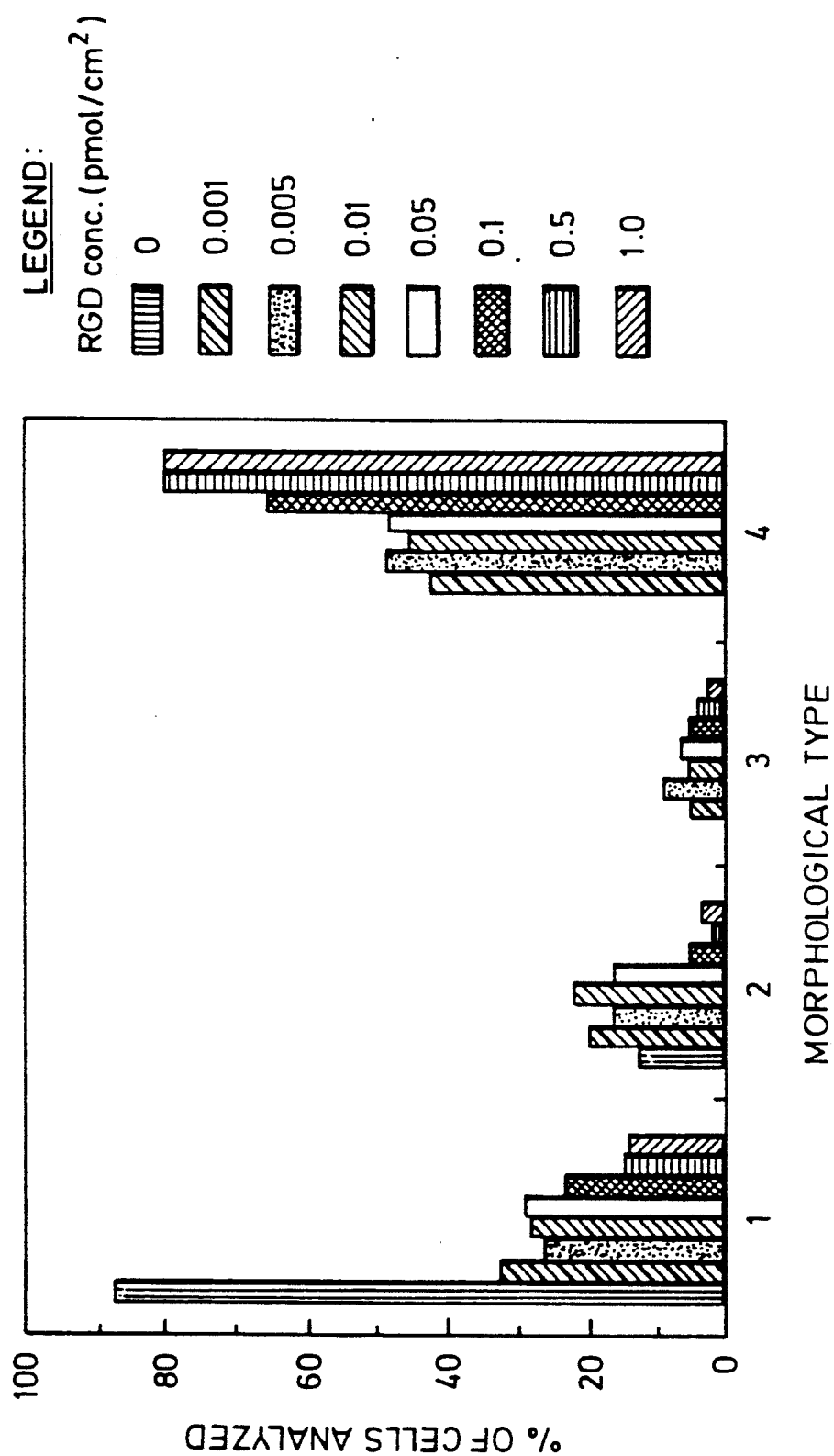
FIG. 18 shows the effects of RGD-peptide density on cell (HFF) spreading.

Derivatized glass surfaces were prepared according to the method described in example 6 employing the GRGDY peptide, except that the amount of peptide added to the tresyl activated glass was less than the 12 picomoles/cm$^2$. This allowed the formation of substrates with known peptide surface densities. The linear region of FIG. 9, referenced in Example 6, indicates that the amount of peptide added to the reactive glass is equal to the amount of peptide coupled to the glass, so long as that amount is less than or equal to 12 picomoles/cm$^2$. Peptide was covalently attached to the derivatized glass as surface concentrations of 0.001, 0.005, 0.01, 0.05, 0.1, 0.5, and 1.0 picomoles/cm$^2$. Human foreskin fibroblasts were seeded on the material in DMEM containing heat inactivated albumin as the only protein and cell spreading was determined after a 4 hour incubation. Cells were graded for morphology of spreading according to the following scheme: rounded cell, no filopods, stage 1; rounded cell, one filopod, stage 2; rounded cell, more than one filopod, stage 3; flattened cell with pseudopods, and polygonal-shaped fully spread cell, stage 4. The results are shown in FIG. 18 and indicate that levels as low as 0.001 picomole/cm$^2$ are sufficient to promote nearly a full spreading response; this is particularly evident from the data on stage 4 cells, where 0.001 picomoles/cm$^2$ resulted in 42% of cells in stage 4 while 1.0 picomoles/cm$^2$ resulted in 81% of cells in stage 4. Thus the cellular response depends upon the peptide surface density, but 0.001 picomoles/cm$^2$ is sufficient to give a strong (about half-maximal) response to the surface.

EXAMPLE 14—GLYCOPHASE GLASS—A MODEL CELL NONADHESIVE SUBSTRATE TO WHICH PEPTIDES CAN BE COUPLED

This example is included to illustrate that glycophase glass is poorly cell adhesive. It, when combined with Examples 15-19, illustrates the advantageous cell-type specificity that can be obtained when peptides are attached to otherwise cell nonadhesive or poorly cell adhesive substrates.

Glycophase glass was prepared by the method of Example 6. Cell spreading on this surface was measured both in the absence and presence of serum, and the results are tabulated below. The cells were human foreskin fibroblasts (HFF), human umbilical vein endothelial cells (HUVEC), human blood platelets (Plt), and human blood platelets prestimulated with 5 μm adenosine diphosphate (Prestim Plt). HFFs and HUVECs were harvested nonenzymatically with a PBS solution containing 54 nM EGTA, centrifuged, and resuspended in normal culture medium or medium containing 2 mg/ml of heat-inactivated serum for serum-free spreading assays. To determine the extent of cell spreading, cells were incubated on the substrates for 4 hours and the percent of spread cells was determined by previously described methods. Platelet spreading was determined by adding PRPP to each substrate and visualizing platelets with 1000X modulation contrast (Hoffman) optics after a 10 minute incubation period. For prestimulated platelets, 5 μM ADP was added to PRP prior to incubation on the substrates. Results are shown in Table 3.

TABLE 3

| Cell type | % Spread with serum | % Spread without serum |
|---|---|---|
| HFF | 9 | 1 |
| HUVEC | 8 | 1 |
| Plt | 0 | N.D. |
| Prestim Plt | 0 | N.D. |

EXAMPLE 15—GLYCOPHASE GLASS COUPLED WITH RGD MATERIALS WHICH SUPPORT THE ADHESION OF FIBROBLASTS AND ENDOTHELIAL CELLS BUT NOT PLATELETS

The peptide GRGDY was coupled to the glycophase glass surface as described in Example 6. Cell spreading assays were performed as described in Example 14. Cell spreading was measured and is reported in Table 4. This material may have advantages for vascular grafts, where the invasion of endothelial cells is desirable but attachment of platelets is detrimental.

TABLE 4

| Cell type | % Spread with serum | % Spread without serum |
|---|---|---|
| HFF | 80 | 81 |
| HUVEC | 62 | 55 |
| Plt | 0 | N.D. |
| Prestim Plt | 0 | N.D. |

EXAMPLE 16—GLYCOPHASE GLASS COUPLED WITH YIGSR MATERIALS WHICH SUPPORT THE ADHESION OF FIBROBLASTS AND ENDOTHELIAL CELLS BUT NOT PLATELETS

The peptide GYIGSRY was coupled to a glycophase glass surface. YIGSR is a sequence in the CAM laminin which promotes cell adhesion (Graf et al., 1987, Cell, 48:989–996). Cell spreading was measured by procedures described in Example 14. This material may have advantages for vascular grafts, where the invasion of endothelial cells is desirable but the attachment of platelets is detrimental. The results are shown in Table 5.

TABLE 5

| Cell type | % Spread with serum | % Spread without serum |
|---|---|---|
| HFF | 64 | 59 |
| HUVEC | 79 | 73 |
| Plt | 0 | N.D. |
| Prestim Plt | 0 | N.D. |

EXAMPLE 17—GLYCOPHASE GLASS COUPLED WITH PDSGR—MATERIALS WHICH SUPPORT THE ADHESION OF FIBROBLASTS AND ENDOTHELIAL CELLS BUT NOT PLATELETS

The peptide GPDSGRY was coupled to a glycophase glass surface. PDSGR is a sequence discovered in laminin which has cell adhesion-promoting activities (Kleinman et al. 1989, Arch. Biochem. Biophys., 272:1:39–45). Cell spreading was measured by procedures described in Example 14. The results are shown in Table 6. This material may have advantages for vascular grafts, where the invasion of endothelial cells is desirable but the attachment of platelets is detrimental.

TABLE 6

| Cell type | % Spread with serum | % Spread without serum |
|---|---|---|
| HFF | 66 | 64 |
| HUVEC | 66 | 50 |
| Plt | 0 | N.D. |
| Prestim Plt | 0 | N.D. |

EXAMPLE 18—GLYCOPHASE GLASS COUPLED WITH REDV—MATERIALS WHICH SUPPORT THE ADHESION OF ENDOTHELIAL CELLS BUT NOT FIBROBLASTS OR PLATELETS

The peptide GREDVY was coupled to a glycophase glass surface. The sequence REDV, which was derived from fibronectin sequence information, was shown to promote b16-f10 cell adhesion but not BHK fibroblast adhesion by Humphries et al. (1986 J. Cell Bio., 103:6 2637–2647). Cell spreading was measured by procedures described in Example 14. The results are shown in Table 7. This material may have advantages for vascular grafts, where the invasion of endothelial cells is desirable but the invasion of fibroblasts and vascular smooth muscle cells and the attachment of platelets is detrimental.

TABLE 7

| Cell type | % Spread with serum | % Spread without serum |
|---|---|---|
| HFF | 9 | 2 |
| HUVEC | 79 | 69 |
| Plt | 0 | N.D. |
| Pretim Plt | 0 | N.D. |

EXAMPLE 19—GLYCOPHASE GLASS COUPLED WITH IKVAV MATERIALS WHICH DO NOT SUPPORT HUVEC OR PLATELET SPREADING, BUT SHOULD SUPPORT NEURITE OUTGROWTH

The peptide GIKVAVY was coupled to a glycophase glass surface. The sequence IKVAV, which was derived from laminin sequence information, was shown to promote cell adhesion but no spreading of several cell types and neurite outgrowth of neuronal cell types by Tashiro et al. (1989 J. Bio. Chem., 264:27 16174–16182). Cell spreading was measured by procedures described in Example 14. The results are shown in Table 8. This material may have advantages for implants in nervous tissue, where the invasion of neurons and the formation of axonal processes (neurites) is desirable.

TABLE 8

| Cell type | % Spread with serum | % Spread without serum |
|---|---|---|
| HFF | 47.4 | 42.5 |
| HUVEC | 11.2 | 0 |
| Plt | 0 | N.D. |
| Prestim Plt | 0 | N.D. |

EXAMPLE 20—POLYETHYLENE TEREPHTHALATE TO WHICH POLYETHYLENE GLYCOL HAS BEEN IMMOBILIZED—A POLYMERIC CELL-NONADHESIVE SUBSTRATE TO WHICH PEPTIDES CAN BE ATTACHED (PET/PEG)

Polyethylene glycol (PEG) of molecular weight 18,500 was immobilized to a polyethylene terephthalate (PET) film using a solution processing technique described later herein. The resulting film (PET/PEG) was much more wettable than the unmodified PET and did not support the attachment and spreading of cells. The PET/PEG films were extracted in dioxane for 10 minutes as a control for the solvent used in the peptide grafting procedures. Human vascular smooth muscle cells (HVSMC) were also included when these PET/PEG-based materials were tested, because this cell type is found in vascular tissues and can interact with vascular implants. The percentage of spread cells was determined by the procedures described in Example 14. The results are shown in Table 9. HFF, HUVEC, and HVSMC spreading was determined in the presence of serum-supplemented medium.

TABLE 9

| Cell Type | % Spread with serum |
|---|---|
| HFF | 0 |
| HUVEC | 0 |
| HVSMC | 0 |
| Plt | 0 |
| Prestim Plt | 0 |

EXAMPLE 21—PET/PEG COUPLED WITH RGD-MATERIALS WHICH SUPPORT THE ADHESION OF FIBROBLASTS AND ENDOTHELIAL CELLS BUT NOT PLATELETS OR VASCULAR SMOOTH MUSCLE CELLS

The peptide GRGDY was covalently coupled to the PET/PEG surface of Example 20 using the same chemistry as in Example 15. HFF, HUVEC, and HVSMC spreading was determined in the presence of serum-supplemented medium. Cell spreading was as shown below in Table 10. This material may have advantages for vascular grafts, where the invasion of endothelial cells is desirable but the attachment of platelets is detrimental.

TABLE 10

| Cell Type | % Spread with serum |
|---|---|
| HFF | 100 |
| HUVEC | 71 |
| HVSMC | 0 |
| Plt | 0 |
| Prestim Plt | 0 |

EXAMPLE 22—PET/PEG COUPLED WITH REDV-MATERIALS WHICH SUPPORT THE ADHESION OF ENDOTHELIAL CELLS BUT NOT FIBROBLASTS OR PLATELETS OR VASCULAR SMOOTH MUSCLE CELLS

The peptide REDV was coupled to the PET/PEG surface of Example 20. HFF, HUVEC, and HVSMC spreading was determined in the presence of serum-supplemented medium. Cell spreading was as shown below in Table 11. This material may have advantages for vascular grafts, where the invasion of endothelial cells is desirable but the invasion of fibroblasts and vascular smooth muscle cells and the attachment of platelets is detrimental.

TABLE 11

| Cell Type | % Spread with serum |
|---|---|
| HFF | 0 |
| HUVEC | 78 |
| HVSMC | 0 |
| Plt | 0 |
| Prestim Plt | 0 |

EXAMPLE 23—PET/PEG COUPLED WITH IKVAV-MATERIALS WHICH DO NOT SUPPORT HUVEC OR PLATELET SPREADING, BUT SUPPORTS HFF SPREADING AND SHOULD SUPPORT NEURITE OUTGROWTH

The peptide GIKVAVY was coupled to the PET/PEG surface of Example 20. The sequence IKVAV, which was derived from laminin sequence information, was shown to promote cell adhesion but no spreading of several cell types and neurite outgrowth of neuronal cell types of Tashior et al. (1989 J. Bio. Chem., 264:27 16174–16182). Cell spreading was measured by procedures described in Example 14 and is shown in Table 12. This material may have advantages for implants in nervous tissue, where the invasion of neurons and the formation of axonal processes (neurites) is desirable.

TABLE 12

| Cell Type | % Spread with serum |
|---|---|
| HFF | 100 |
| HUVEC | 0 |
| Plt | 0 |
| Prestim Plt | 0 |

EXAMPLE 24—A SOLUTION TECHNIQUE TO INCORPORATE POLYETHYLENE OXIDE AND OTHER WATER SOLUBLE POLYMERS INTO SURFACES OF POLYMERIC BIOMATERIALS

Currently used biomedical polymers in applications involving blood contact have not proved to be sufficiently nonthrombogenic to be useful in small diameter vascular grafts. Adhesion of platelets and other blood cells is the main cause of low patency of small diameter grafts, and an aspect of the present embodiment is to reduce the interactions of blood components with biomedical polymers. Because the adhesion of platelets, white blood cells, fibroblasts, etc. is mediated by the adsorption of proteins to the polymer surface, an approach was adopted which reduced the interaction of proteins with these polymers.

Polyethylene oxide (PEO) surfaces have been observed to resist the adsorption of plasma proteins as a result of their strong hydrophilicity, chain mobility and lack of ionic charge [25]. Several groups have used PEO or PEG (polyethylene glycol) as a modifier in a quest to obtain a biocompatible or nonadhesive surface. Different approaches have been used to modify polymer surfaces with PEO. Among them are those techniques that involve covalent grafting of PEO to a base polymer such a PET [26,27], a polyurethane [28], or polyvinyl alcohol [29], polymerization of a monomer having a pendant PEO chain [30,31], incorporation of PEO into a base polymer by block copolymerization [32,33], or direct adsorption of PEO-containing surfactants which are typically block copolymers of the AB or ABA type where one of the blocks is a PEO [25,34]. Most of these techniques have utilized PEO of relatively low molecular weights (less than 5000 daltons) and only a few have used significantly higher molecular weights [26,27,34].

Although some of the above described techniques work reasonably well in reducing cellular interactions at the surfaces of the modified polymers, most of them require multiple stages to obtain the necessary surface modification. Furthermore, they are limited by the structure and availability of labile chemical moieties on the base polymer surface and are in many cases, specific for modification of the base polymers.

Figure 19:
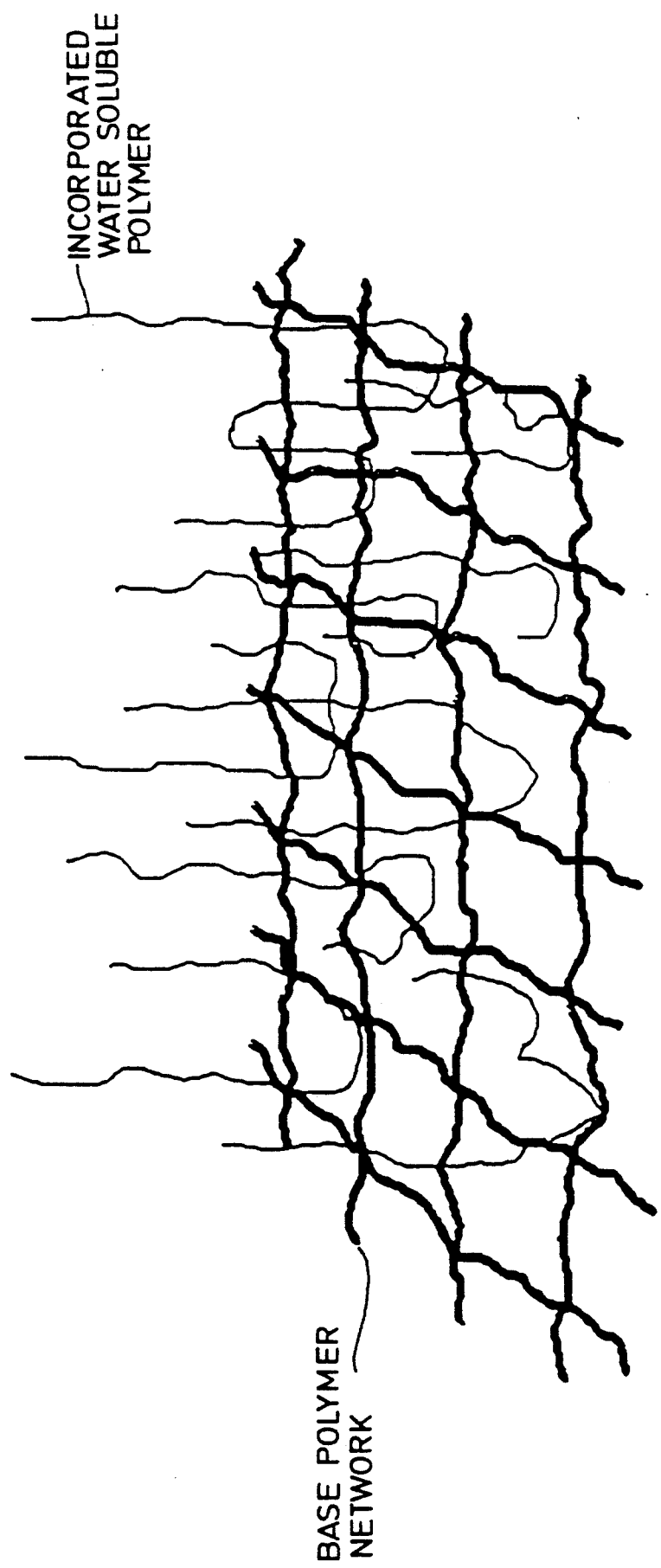
FIG. 19 is a schematic of proposed surface structure of the Physical Interpenetrating Network (PIPN).

The present invention relates to a technique incorporating PEO and other water-soluble polymers (WSP) into the surface of a base polymer (BP). This technique is of general applicability and is limited only by the solution properties of the BP in a solvent that also dissolves the WSP to be incorporated into its surface. The technique involves immersing the polymeric device or material (fabricated from the BP) to be modified into a liquid that is a mutual solvent for the BP and the WSP. The interface between the BP and the liquid then begins to soften and results in the loosening of the polymer network on the surface of the BP. During this time the molecules of the WSP are free to diffuse into the semi-dissolved interface. After a period of time the system is quenched with water which is a nonsolvent for the BP but is mutually soluble with the immersion solvent. This results in a rapid collapse of the interface, entrapping the chains of the WSP within the BP network. In this way the BP is noncovalently but stably modified with the WSP. Alternate quenching solvents could also be used rather than water, where the quenching solvent is a solvent for the WSP but not for the BP. Examples of alternate quenching solvents include but are not limited to methanol, ethanol, acetone, dimethyl, formamide, tetrahydrofuran and benzene for the PET TIENs; and ethanol and methanol for the PMMA PIPNs. Alternatively a mutual nonsolvent for both the WSP and BP could be used to quench and could be followed by a rinse by a solvent for the WSP but not the BP. Alternatively the system may be dried and then rinsed in quenching solvent to remove the excess solvent. A schematic of the proposed entrapment of WSP chains in the BP is shown in FIG. 19. The conditions of the entrapment process, such as appropriate solvent dilution (to prevent the BP from dissolving entirely), concentration of the WSP, and treatment time, of course need to be optimized to obtain a suitably modified stable physical interpenetrating network (PIPN). It also follows that the molecular weight of the WSP should be of some importance because molecules with relatively short chain lengths (i.e., low molecular weights) cannot be effectively entrapped by the collapsing network on the BP and in due course may succeed in diffusing out of the network. By the same token, very large molecules (i.e., high molecular weights) have mass transfer limitations and are not incorporated into the surface of the BP effectively.

A technique has been described in the literature [35] which stresses only the use of diblock surfactant copolymers where one block is hydrophobic and the other hydrophilic. That the technique may have applications in biomaterials is mentioned but no data or examples are presented. The technique of the present invention is generally applicable to any homopolymer to be incorporated into a BP surface and as such is not limited to diblock copolymers with surfactant properties.

MATERIALS AND METHODS

Preparation of a physical interpenetrating network PIPN on PET.

Thin films of PET (Mylar, Du Pont) were used for surface modification using the PIPN technique to incorporate PEO (of molecular weights 5000, 18500, and 100000 g/mol, Polysciences, Inc.), PVP (mol. wt. 24000 g/mol, Aldrich Chemical Co.) and PEOX (mol. wt. 439000 g/mol, Dow Chemical Co., # XA10874.05). The PET films were extracted in acetone for at least 24 hours at room temperature before use. Trifluoroacetic acid (TFAA, Morton Thiokol, Inc.) was used as the treatment solvent since it dissolved all the WSPs as well as PET. Full strength TFAA was found to dissolve the PET very rapidly and hence needed dilution in order that the BP be treated for a sufficient length of time. Solutions of the WSPs were made in deionized and filtered water (DIFW) at concentrations of 0.4 g/ml except for the PEO 100000 and PEOX which were used at 0.2 g/ml due to high viscosity. It was found that dilution of TFAA by 18-20% was suitable to prevent dissolution of the PET film and retain optical clarity after quenching with water. TFAA was diluted to the suitable concentration by adding the aqueous WSP solutions. The PET films were then added to the solution of the WSP in diluted TFAA and allowed to stand for 30 minutes with periodic swirling at room temperature. The mixture was then rapidly quenched with a large excess of DIFW to produce the PIPN. The films were then transferred to DIFW in which they were stored. The water was changed periodically to remove any WSP that may have leached out of the BP surface. A control was also run with the same dilution of TFAA with DIFW but without any WSP.

Preparation of PIPN on Pellethane.

Pellethane (Dow Chemical Co., # 2363-80AE) was obtained as pellets. A solution of pellethane in tetrahydrofuran (THF) at a concentration of 50 g/l was used to cast films of 50 mil thickness using a casting knife. These films were cured in an oven at 60°-70° C. following casting to evaporate the solvent. A number of different solvents were tried and THF was found to be suitable for generation of the PIPN on pellethane. The PIPN was made only using the PEO 18500 WSP for reasons explained below. From control runs (i.e., solvent dilutions without any WSP) it was found that dilution of THF to 40% with DIFW was necessary to retain structural integrity and optical clarity of the film upon quenching. The PEO 18500 was insoluble in THF at room temperature but was soluble at 60° C., hence the surface modification procedure for pellethane was performed at this temperature. The treatment solution consisted of 40% THF, 20% of the PEO 18500 solution in water, and the remaining 40% DIFW. This mixture was heated to 60° C. until the PEO dissolved and the pellethane films immersed in the solution for 15-25 minutes. The procedure was carried out at 60° C. in an oven. The solution was then quenched with an excess of DIFW and the treated films transferred to water for storage. A control was also run at the same THF dilution without the presence of PEO.

Preparation of PIPN on PMMA.

PMMA (medium mol. wt., Aldrich Chemical Co.) was obtained as a powder. It was dissolved in acetone at 50 g/l and a film cast similar to the one for pellethane. Acetone was used as a modification solvent for PMMA. It was found that a dilution of acetone to 60% was suitable for the procedure. The treatment solution consisted of 60% acetone, 20% of the aqueous PEO 18500 solution (40% PEO in water), and the remaining 20% water. The treatment was performed at room temperature for 15-25 minutes followed by quenching with water. The modified films were once again stored in water that was changed periodically. Controls samples were also run.

Surface Analysis and Characterization.

Contact angles on the modified surfaces were measured in a custom built device. Air contact angles were measured under water to determine any change in hydrophilicity following the modification procedure.

ESCA analysis (VG Instruments, UK) on the polymer surfaces was performed to determine the presence of the WSP on the BP surface after the modification procedure.

Measurement of Biological Responses on PIPN Surfaces.

Protein adsorption studies on the modified surfaces were done using albumin (BSA, Sigma). The protein was radiolabelled with $I^{125}$ NaI (ICN Biomedicals, Inc.) using the iodobead technique [36]. The specific activity of the labelled albumin was found to be 53.9 μCi/mg. Small films (0.5×0.5 cm²) were cut from the modified polymers and incubated with radiolabelled albumin at a concentration of 0.094 mg/ml in phosphate-buffered saline (PBS) for 4 hours at 37° C. Following the incubation the films were rinsed with a non-radiolabelled albumin solution in PBS of the same concentration as the adsorption solution and the films counted in a gamma counter (Isoflex, ICN Micromedic Systems) for adsorbed protein. All samples were done in quadruplet.

Figure 20:
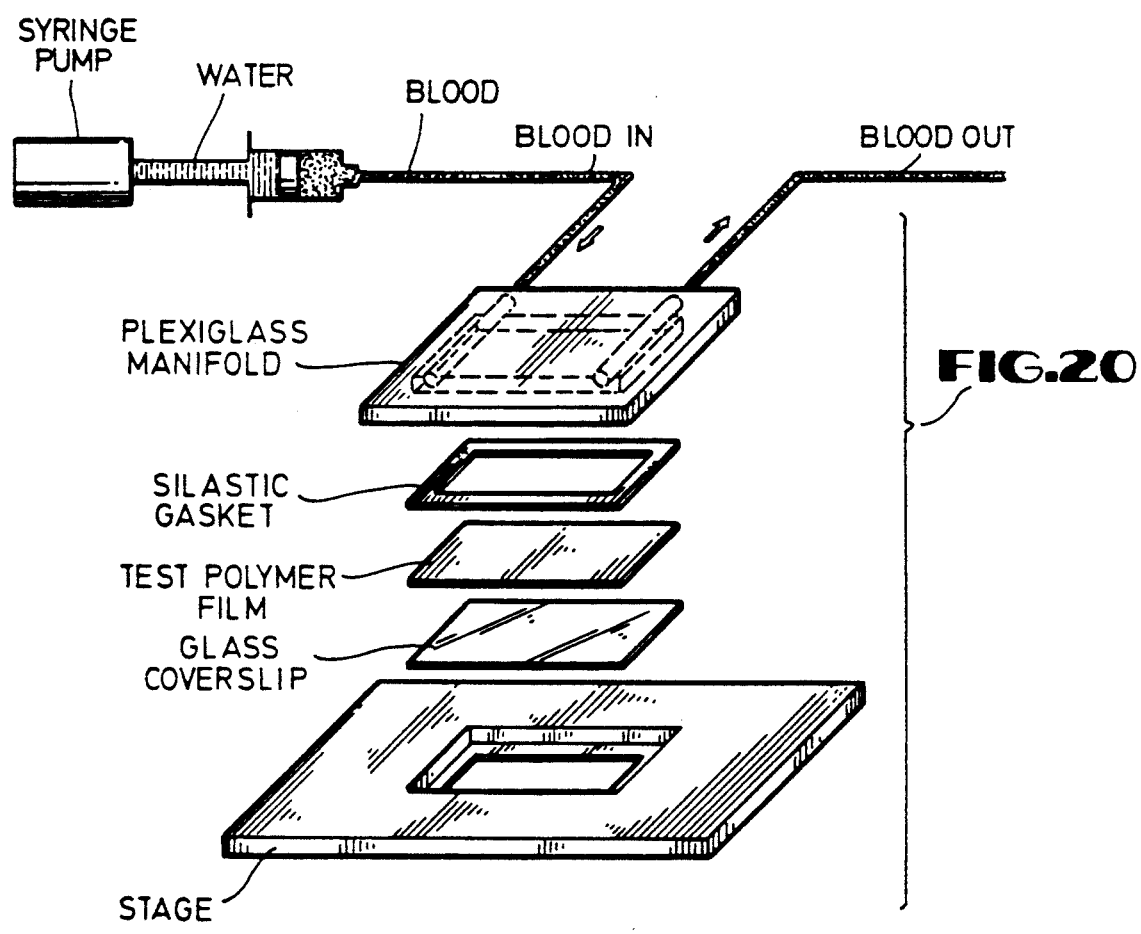
FIG. 20 is an exploded view of flow chamber used for in vitro online visualization of platelet adhesion to modified polymer surfaces.

Short-term blood compatibility was studied in a parallel-plate flow chamber that provided the necessary controlled flow and shear environment needed for this study. The flow chamber is shown in FIG. 20. The surface modified films were mounted on glass coverslips (24×50 mm) which formed the base of the flow chamber. All nonrelevant surfaces were coated with albumin (4 g/dl, in HEPES buffer) prior to blood contact to avoid preactivation of platelets before contacting the test material surface. Freshly drawn heparin-anticoagulated (2 units/ml) human whole blood was used in these studies. Platelets were labelled with a fluorescent dye, mepacrine (10 μM), at the time of venipuncture. Epifluorescence microscopy and digital image processing were used to visualize platelet adhesion and thrombus formation during flow and to determine adherent platelet counts on the tested surfaces. The image acquisition system has been described elsewhere [37,38]. Blood flow was maintained for 10 minutes at a wall shear rate of 100 sec$^{-1}$.

Following blood flow over the modified polymer surfaces, the films were gently rinsed in phosphate buffered saline (PBS) and then fixed in 2.5% solution of glutaraldehyde in PBS overnight. The blood contacting surfaces were then subjected to scanning electron microscopy (SEM) to evaluate platelet adhesion as well as morphology of adhered platelets to assess the degree of spreading and activation of the platelets on the different surfaces.

As a further, more rigorous test of the effectiveness of PEO and other WSPs in preventing cell adhesion to the modified polymer surfaces, cell culture of human foreskin fibroblasts (HFF) was performed on these surfaces. Adhesion and spreading assays were done to determine the effectiveness of these surfaces in reducing protein adsorption and hence adhesion and spreading of these cells on the modified polymers.

RESULTS AND DISCUSSION

Measurement of contact angles on the modified surfaces gave an indication of the relative hydrophilicity of these surfaces before and after the modification procedure. All polymers were extracted in water for at least one week before any measurements were made. Table 13 shows the contact angle data on the PET modified surfaces. Table 14 shows the contact angle data on Pellethane and Table 15, the data for PMMA.

TABLE 13

| Contact angles for modified PET surfaces. | |
|---|---|
| MODIFICATION | CONTACT ANGLE, (°) |
| PET-untreated | 65.3 ± 0.9 |
| PET-control | 50.5 ± 2.8 |
| PET-PEO5000 | 14.9 ± 2.8 |
| PET-PEO18500 | 19.4 ± 3.6 |
| PET-PEO100000 | 21.1 ± 2.3 |
| PET-PVP24000 | 20.6 ± 2.8 |
| PET-PEOX439000 | 22.2 ± 2.4 |

TABLE 14

| Contact angles for modified Pellethane surfaces. | |
|---|---|
| MODIFICATION | CONTACT ANGLE, (°) |
| PELL untreated | 47.9 ± 3.1 |
| PELL control | 35.2 ± 2.7 |
| PELL-PEO18500 | 24.6 ± 4.3 |

TABLE 15

| Contact angles for modified PMMA surfaces. | |
|---|---|
| MODIFICATION | CONTACT ANGLE, (°) |
| PMMA untreated | 59.6 ± 3.0 |
| PMMA control | 37.0 ± 3.3 |
| PMMA-PEO18500 | 22.3 ± 1.8 |

Decreasing contact angles indicate increasing hydrophilicity of the polymer surfaces. PET-untreated represents the virgin polymer that has only been extracted in acetone. The control PET shows a smaller contact angle than the untreated polymer indicating that the treatment with TFAA actually increases its hydrophilicity to a small extent. The WSP treated films show a much increased hydrophilicity indicating the presence of the respective WSPs at the surface of the PET.

Contact angle data on Pellethane (PELL) shows the same trend as for the PET surfaces. The PEO 18500 modified pellethane shows a similar contact angle to the corresponding PET surface. Once again the same trend is obtained on PMMA. Thus all the WSP-modified surfaces have contact angles very close to each other indicating similar degrees of hydrophilicity and similar interfacial energies.

Figure 21:
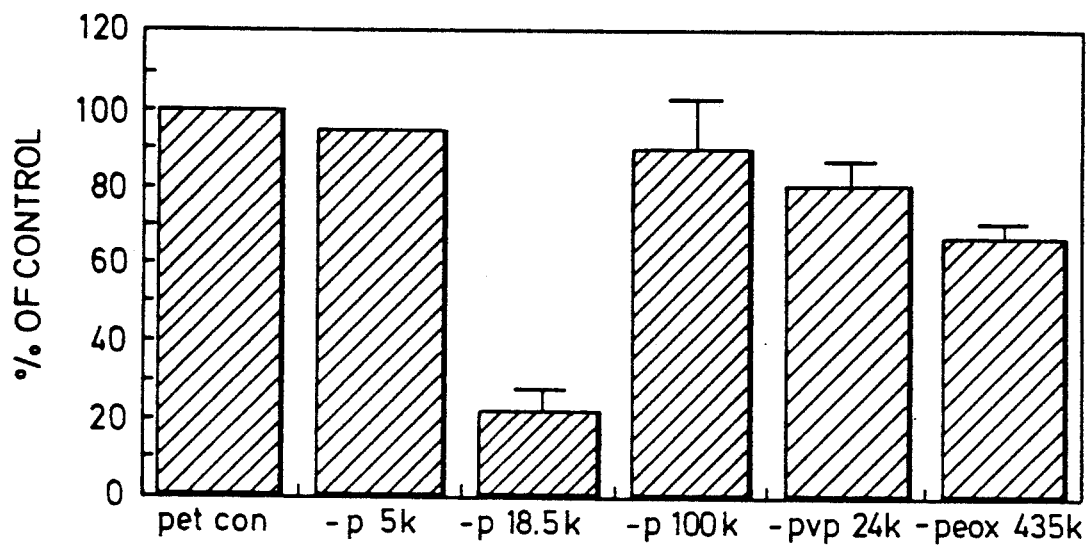
FIG. 21 shows $I^{125}$ albumin adsorption to modified PET surfaces showing low levels of adsorption on the surface modified with PEO 18500.

An analysis of radiolabeled albumin adsorption on the modified PET surfaces gave the results shown in FIG. 21. The data clearly shows a sharp drop in albumin adsorption only for the surface modified with PEO 18500. An approximately 80% decrease in adsorption over the control is observed for this surface. The PVP modified surface shows a decrease of about 20% and the PEOX modified surface shows a decrease of approximately 30% over the control. The PEO 5000 and 100000 modified surfaces do not show significantly different adsorption levels. This data may indicate that the PEO 5000 is not of a large enough molecular weight to prevent protein adsorption at the polymer surface, and that the PEO 100000 is too bulky to be effectively integrated into the polymer surface in a configuration that enables it to prevent adsorption of protein.

Figure 22:
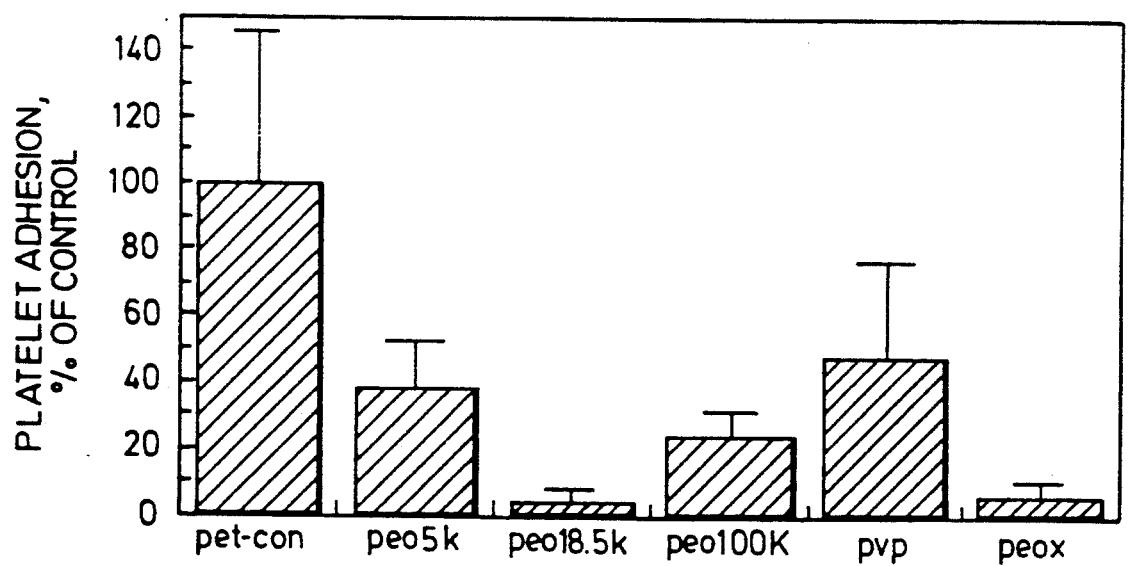
FIG. 22 shows platelet adhesion on PET PIPN's as obtained by fluorescence videomicroscopy. The control value of 100% corresponds to 46.25 platelets/ 1000 $\mu m^2$ of the polymer surface.

An analysis of platelet adhesion to the modified PET surfaces as obtained by epifluorescence videomicroscopy during flow of whole blood over the polymer surfaces is shown in FIG. 22. The PEO 18500 modified surface shows a reduction in platelet adherence to about 5% of the control value. The PEOX modified surface also shows a significant reduction to about 10% of control levels. The PEO 100000 modified surface shows a reduction to about 30%, the PEO 5000 and PVP modified surfaces show a reduction to 40–80% of control values. This correlates well with the protein adsorption data on the PEO 18500 modified PET. The significantly low platelet adherence on the PEOX modified PET has not been explained.

Adhesion and spreading of human foreskin fibroblasts in Dulbecco's Modification of Eagle's Medium (DMEM) supplemented with 10% fetal calf serum was used as a test of the effectiveness of the WSP modified surfaces in preventing protein adsorption. The cells were seeded at a known density on the PET, pellethane and PMMA modified surfaces and the number of spread cells were counted first at four hours after seeding and periodically thereafter until they reached confluency.

Figure 23:
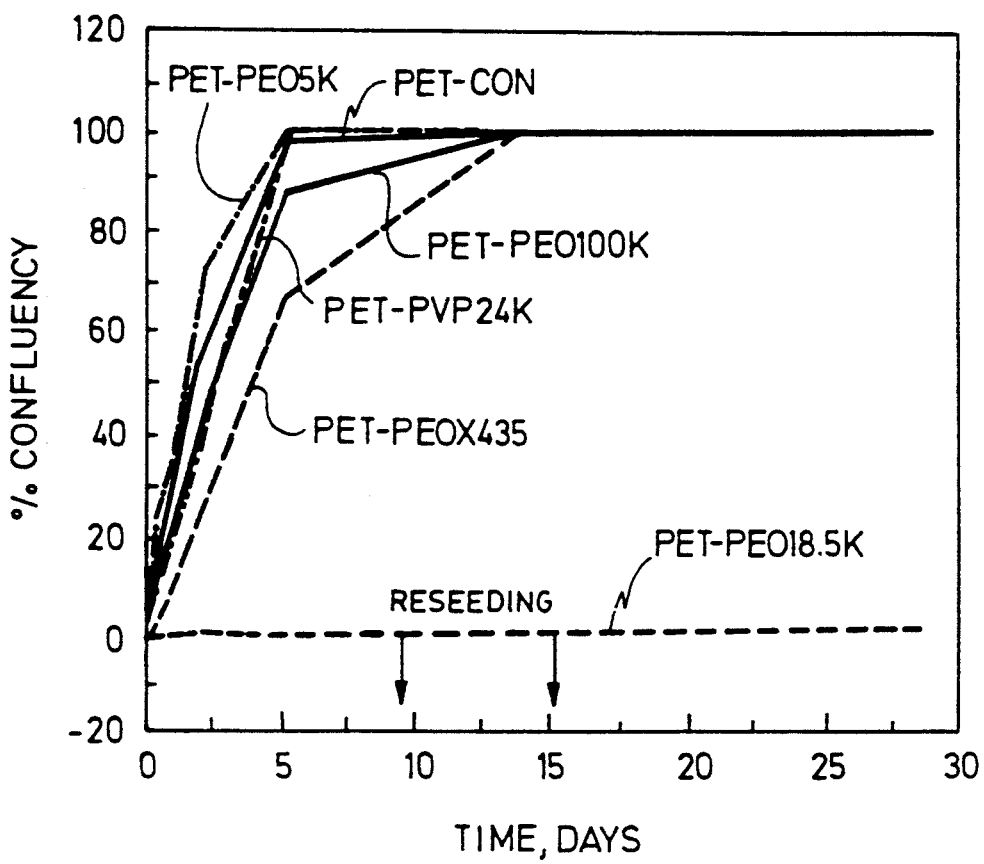
FIG. 23 shows cell spreading assays on PET PIPN's over 30 days in culture. Cells were seeded at a concentration of 30000/$cm^2$. The PEO 18500 modified surface was reseeded at 9 and 15 days following the initial seeding.

The PET modified films were seeded with 30000 cells/cm$^2$ after extraction in water for 25 days. The most dramatic results were obtained here for the PEO 18500 modified surface on PET. As can be seen in FIG. 23, all the surfaces except the one modified with PEO 18500 modified PET reached confluency within 5-10 days after initial seeding. In spite of reseeding the PEO 18500 on day 9 and again on day 15, the cells do not adhere to this surface even after more than 30 days in culture. Among the surfaces that reach confluency, the PEOX modified surface is the slowest to respond but eventually reaches confluency. These results are in strict concordance with the data obtained from protein adsorption and platelet adhesion experiments. The results for the PEOX surfaces may indicate that in a blood contacting application, such a surface may behave suitably in the short-term but over longer contact times, eventually may turn thrombogenic.

Figure 24:
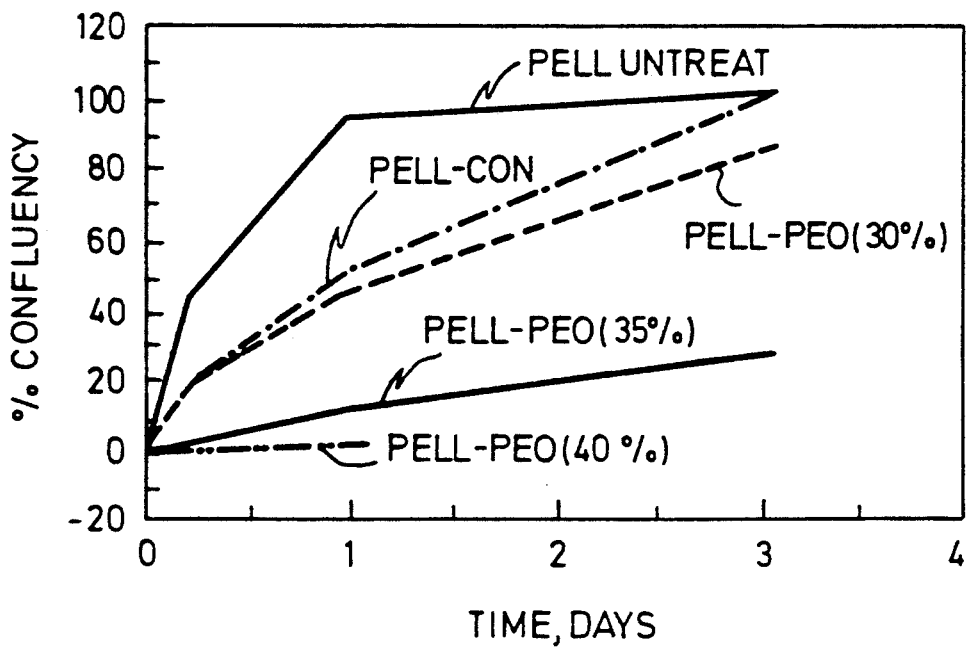
FIG. 24 shows cell spreading assays on Pellethane PIPN's. Cells were seeded at a concentration of 70000/$cm^2$. These surfaces were modified only with PEO 18500. The numbers in parentheses indicate the strength of THF used for the modification procedure.
Figure 25:
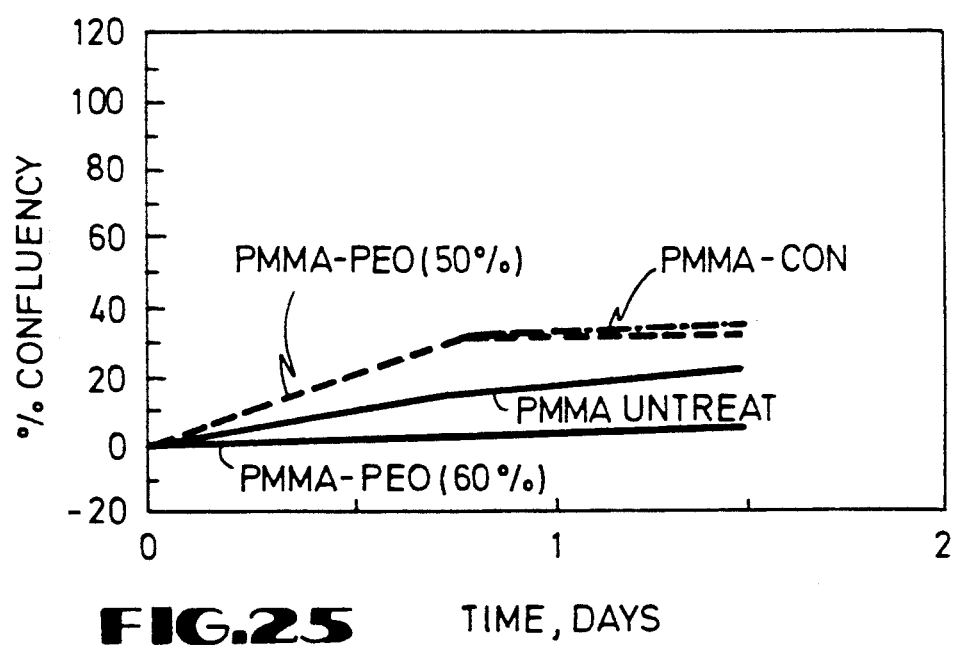
FIG. 25 shows cell spreading assays on PMMA PIPN's. Cells were seeded at a concentration of 70000/$cm^2$. These surfaces were modified only with PEO 18500. The numbers in parentheses indicate the strength of Acetone used for the modification procedure.

These results indicate the effectiveness and suitability of PEO 18500 in preventing protein adsorption and hence cellular interactions when impregnated into a polymer surface in the form of a PIPN. As a consequence of these results it was decided to modify the surfaces of Pellethane and PMMA only with PEO 18500 and reconfirm the earlier results on PET. Having determined the suitable conditions, solvents, etc., these polymers were impregnated with PEO 18500 to obtain a PIPN on these surfaces. Cell were seeded on these modified surfaces under more rigorous conditions, (i.e., 2.5 times the PET seeding density). Under these conditions, a reasonably adhesive substrate such as the untreated PET would reach confluency in less than 2 days. The results obtained for Pellethane are shown in FIG. 24 and those for PMMA in FIG. 25. Once again, PEO 18500 is successful in reducing cell spreading and growth on these substrates. It is seen that as the concentration of the treatment solvent is increased, the cell adherence decreases indicating a better incorporation of PEO 18500 into the base polymer.

Similar surface hydrophilicities on the different modified surfaces resulted in vastly differing cellular responses, indicating that surface mobility and a suitable chain length of the incorporated polymer are important factors determining the outcome of cellular interactions at a polymer surface.

These results indicate the general applicability of the PIPN technique to modification of polymer systems and moreover, the extraordinary ability of PEO 18500 to inhibit protein adsorption and hence cellular interactions at a biomaterial surface. The potential of this technique in application to existing biomedical polymers is enormous. Being a simple solution process, prefabricated devices may be modified simply by immersion in a suitable solution of the WSP and then transfer to a nonsolvent for the device material such as water.

The PIPN appears to be quite stable over a period of at least several weeks. The cell adhesion and protein adsorption experiments with the PEO 18500 modified surfaces (which showed low cell adherence and protein adsorption) were done 25 days and 20 days respectively, after the preparation of these PIPNs. During this 20-25 day period they were continually extracted in water.

Potential applications of this process and the water soluble polymer PEO (PEG) (preferably of molecular weight 18500) include areas involving blood-contacting biomaterials, such as vascular grafts, catheters and pacing leads. In addition, the labile PEO end groups on these modified polymer surfaces could serve as a site for attachment of suitable biospecific peptides (described elsewhere herein) to produce surfaces that would adhere only particular cell types. For example, endothelial cells might be adhered in case of application as a vascular graft. About half of the vascular grafts currently marketed are made from Dacron (PET) which is the major focus of this example. Other applications involve materials in contact with tissue where cell adhesion is not desired, such as biosensor membranes, intraocular lenses (PMMA). Materials may also be produced for use with protein affinity chromatography, where non-adsorbing supports are preferred for attachment of specifically adsorbing ligands. Non-adsorbing tubes and bags might also be useful in other areas of protein and blood processing. The technique of the present invention may have application in the manufacture or treatment of ultrafiltration membranes for use in biotechnology and food processing. Nonbiological applications may also exist, such as piping systems for very clean water systems (e.g., as used in the microelectronics industry) and perhaps in marine non-fouling surfaces.

Further studies are planned concerning fibrinogen adsorption on the PET surfaces, and albumin and fibrinogen adsorption on PMMA and Pellethane surfaces; ESCA data showing the presence of PEO or other WSPs on these surfaces; blood contact for Pellethane and PMMA surfaces as well as SEM analysis following blood contact to assess morphology of platelets on these surfaces; and finally further in vivo tests such as subdermal implantation in mice. Preliminary data on PET-PEO 18500 showed it to be effective in preventing cell adherence. A one week control PET implant showed extensive fibrosis and encapsulation while the corresponding PET surface modified with PEO 18500 was found to be free floating with minimal cellular adherence.

The following references, as well as those cited elsewhere are incorporated in pertinent part by reference herein for the reasons cited.

BIBLIOGRAPHY

1. Grinnell, F. (1978), "Cellular Adhesiveness and Extracellular Substrata", *International Review of Cytology*, 53: 67-149.
2. Couchman, et al., (1982), *J. Cell Biol.*, 93: 402-410.
3. Pearlstein, E., (1976), *Nature*, 262: 497-500.
4. Kleinman, et al., (1976), *Biochem. Biophys. Res. Commum.*, 72: 426-432
5. Grinnell, F. (1976), *Exp. Cell Res.*, 97: 265-274.
6. Grinnell, F. (1976), *Exp. Cell. Res.*, 102: 51-62.
7. Hynes, et al., (1982), *J. Cell. Biol.*, 95: 369-377.
8. Pierschbacher, et al., (1984), *Nature*, 309: 30-33.
9. Pytela, et al., (1985), *Cell*, 40: 191-198.
10. Pytela, et al., (1985), *Proc. Natl. Acad. Sci. USA*, 82: 5766-5770.
11. Fitzgerald, et al., (1985), *J. Biol. Chem.*, 260: 11366-11374.
12. Ruoslahti, et al., (1987), *Science*, 238: 491-497.
13. Hynes, R. O., (1987), *Cell*, 48: 549-554.
14. Singer, et al., (1987), *J. Cell. Biol.*, 104: 573-584.
15. Cheresh, A. (1987), *Proc. Natl. Acad. Sci. USA*, 84: 6471-6475.
16. Variani, et al., (1986), *In Vivo*, 22: 575-582.

17. Aubert, et al., (1987), *J. Biomed. Mater Res.*, 21: 585–18.

18. Ohlson, et al., (1978) *FEBS Letters*, 93, 5–9.

19. Woods, et al., (1986), *EMBO J.*, 5: 665–670.

20. Streeter, et al., (1987), *J. Cell Biol.*, 105: 507–515.

21. Paul, et al., (1976), *J. Appl. Pol. Sci.*, 20: 609–625.

22. Humphries, et al., (1986), *J. Cell Biol.*, 103: 2637–2647.

23. Mohr and Pommerening, (1985), *Affinity Chromatography: practical and theoretical aspects*, Chapter 4.

24. Costello and McCarthy (1987), *Macromolecules*, 20: 2819–2828.

25. J. H. Lee, J. Kopecek, and J. D. Andrade, *J. Biomed. Mater. Res.* 23, 351, 1989.

26. N. P. Desai and J. A. Hubbell, *Proceedings of the ACS Division of Polymeric Materials: Science and Engineering* 62, 731, 1990.

27. W. R. Gombotz, W. Guanghui, and A. S. Hoffman, *J. Appl. Polym. Sci.* 37, 91, 1989.

28. N. Chisato, K. D. Park, T. Okano, and S. W. Kim, *Trans. Am. Soc. Artif. Intern. Organs* 35, 357, 1989.

29. M. V. Sefton, G. LLanos, and W. R. Ip, *Proceednigs of the ACS Division of Polymeric Materials: Science and Engineering* 62, 741, 1990.

30. S. Nagaoka and A. Nakao, *Biomaterials* 11, 119, 1990.

31. Y. Mori, S. Nagaoka, H. Takiuchi, et al., *Trans. Am. Soc. Artif. Intern. Organs* 28, 459, 1982.

32. E. W. Merrill, E. W. Salzman, S. Wan, et al., *Trans. Am. Soc. Artif. Intern. Organs* 28, 482, 1982.

33. S. K. Hunter, D. E. Gregonis, D. L. Coleman, et al., *Trans. Am. Soc. Artif. Intern. Organs* 29, 250, 1983.

34. C. Maechling-Strasser, Ph. Dejardin, J. C. Galin, and A. Schmitt, *J. Biomed. Mater. Res.* 23, 1385, 1989.

35. J. H. Chen and E. Ruckenstein, *J. Colloid Interface Sci.* 132, 100, 1989.

36. M. K. Markwell, *Anal. Biochem.* 125, 427, 1982.

37. J. A. Hubbell and L. V. McIntire, *Rev. Sci. Instrum.* 57, 892, 1986.

38. N. P. Desai and J. A. Hubbell, *J. Biomaterials Sci., Polym. Ed.* 1, 123, 1989.

We claim:

1. A cell culture substrate containing less than about 45% water comprising a surface with covalently linked peptide at a concentration density of between about 0.001 picomoles and about 50 picomoles/cm², wherein said peptide is attached through an N-terminal amine to a hydroxyl group at the substrate surface, wherein said peptide is at least one peptide selected from the group consisting of:
GRGD; GYIGSRY; GRGDF, GRGDY; GREDV; GYIGSR; GREDVY; and GRGDS;
wherein said substrate is capable of supporting cell focal adhesion formation and cell spreading.

2. The cell culture substrate of claim 1, wherein said peptide is GRGDY, GYIGSRY, GRGD or GYIGSRY.

3. The cell culture substrate of claim 1, or 2, wherein the substrate comprises a ceramic.

4. The cell culture substrate of claim 3, wherein the ceramic is glass.

5. The cell culture substrate of claim 4, wherein the glass comprises glycerol propylsilane-bonded glass.

6. The cell culture substrate of claim 5, wherein the peptide is GRGDY or GYIGSRY.

7. The cell culture substrate of claim 1, wherein said peptide has 4 or 6 amino acid residues.

8. The cell culture substrate of claim 7, wherein the peptide has 4 amino acid residues and is further defined as GRGD.

9. The cell culture substrate of claim 7, wherein the peptide has 6 amino acid residues and is further defined as GYIGSR.

10. The cell culture substrate of claim 7 wherein the peptide is GREDVY.

11. The cell culture substrate of claim 1, wherein the substrate comprises a material selected from the group consisting of:
a ceramic;
a polymer; and
a metal.

12. The cell culture substrate of claim 11 wherein the metal is titanium.

13. The cell culture substrate of claim 1, wherein the substrate comprises a material selected from the group consisting of
a polymer; or
a ceramic.

14. The cell culture substrate of claim 1, wherein the substrate comprises a polymer selected from the group consisting of:
a plastic;
a poly (hydroxyethyl methylacrylate);
a poly (ethylene terephthalate);
a poly (tetrafluoroethylene);
a fluorinated ethylene; and
a poly(dimethyl siloxane).

15. The cell culture substrate of claim 14, wherein the polymer is poly(hydroxyethyl methacrylate).

16. The cell culture substrate of claim 15, wherein the peptide is GRGD.

17. The cell culture substrate of claim 14, wherein the polymer is poly(ethylene terephthalate).

18. The cell culture substrate of claim 17, wherein the peptide is GRGD or GYIGSR.

19. The cell culture substrate of claim 1, wherein the peptide is attached to the substrate at a surface concentration of between about 0.001 picomoles/cm² and about 20 picomoles/cm².

20. The cell culture substrate of claim 1, wherein the peptide is attached to the substrate at a concentration of between 1 picomoles/cm² to 12 picomoles/cm².

21. The cell culture substrate of claim 1 wherein the peptide is GREDV and provides for the selective adhesion of endothelial cells to the substrate.

22. A method of derivatizing a substrate surface comprising:
chemically derivatizing a surface with GREDVY, GRGD or GYIGSR peptide, wherein said peptide is covalently attached through an N-terminal amine to a hydroxyl group on the substrate surface; and
plating cells on the peptide derivatized surface,
wherein the peptide is at a concentration of about 0.001 picomoles/cm² to about 50 picomoles/cm², wherein said substrate supports cell focal adhesion formation and cell spreading.

23. The method of claim 22, wherein the cells are human, murine, insect or porcine cells.

24. The method of claim 23, wherein a hydroxyl group on the surface is activated by exposing the surface to a chemical selected from the group consisting of: glutaraldehyde; cyanuric chloride; sulfonylchloride; cyanogen bromide; and trifluoroethanesulfonyl chloride.

25. The method of claim 22 wherein the cells are human cells.

26. The method of claim 22 or 25 wherein the surface comprises a peptide concentration of between about 0.001 picomoles/cm$^2$ and about 20 picomoles/cm$^2$.

27. The method of claim 22 or 25, wherein the surface comprises a peptide concentration of between about 0.5 picomoles/cm$^2$ and about 20 picomoles/cm$^2$.

28. The method of claim 22 or 25, wherein the surface comprises a peptide concentration of about 12 picomoles/cm$^2$.

29. The method of claim 22, wherein the cells are 3T3 cells, aortic cells, or foreskin cells.

30. The method of claim 22, wherein the cells comprise NIH/3T3 fibroblasts.

31. The method of claim 22, wherein the cells comprise human foreskin fibroblast cells.

32. A cell culture modification method comprising:
activating hydroxyl moieties of a substrate surface; and
covalently coupling an N-terminal amine of a peptide to a hydroxyl group on the substrate surface, wherein said peptide is at least one peptide selected from the group consisting of:
GRGD; GYIGSRY; GRGDF; GRGDY; GREDV; GYIGSR; GREDVY; and
wherein said peptide is included at a concentration density of between about 0.001 picomoles/cm$^2$ to about 50 picomoles/cm$^2$, and wherein said surface is capable of supporting cell focal adhesion formation and cell spreading.

33. The method of claim 32 wherein the surface comprises the cell culture surface of a device selected from the group consisting of:
a tissue-culture flask;
a Petri dish;
microcarriers;
macrocarriers;
fibers;
monolith supports; and
roller bottles.

34. The method of claim 22 or 32, wherein the surface comprises a material selected from the group consisting of:
a ceramic;
a polymer; and
a metal.

35. The method of claim 34, wherein the metal is titanium.

36. The method of claim 34, wherein the surface comprises a polymer.

37. The method of claim 36, wherein a terminal primary amine of a glycine linker arm on the peptide is covalently coupled to the hydroxyl groups of polymer surface by tresyl chloride activation.

38. The method of claim 36, wherein the polymer is poly(hydroxyethyl methylacrylate).

39. The method of claim 32, wherein the peptide of covalently coupled to the substrate surface hydroxyl groups by tresyl chloride activation.

40. A method for derivatizing a substrate surface of poly (hydroxyethyl methacrylate) comprising:
derivatizing the poly (hydroxyethyl methacrylate) surface with GRGD peptides, wherein said peptides are chemically attached by a covalent chemical bond between the N-terminal amine of the peptide and a hydroxyl moiety of the surface; and
plating cells on the peptide derivatized surface,
wherein the GRGD peptide is at a concentration of between about 0.001 picomoles/cm$^2$ to about 50 picomoles/cm$^2$ on the surface, and wherein said substrate supports cell focal adhesion formation and cell spreading.

41. A method for enhancing selective endothelial cell adhesion to a surface comprising covalently attaching GREDV, or GREDVY peptide through the N-terminal amine of the peptide to surface hydroxyl groups on a substrate surface, and plating cells on the surface, wherein said surface supports selective endothelial cell focal adhesion formation and cell spreading.

42. The method of claim 41 wherein the peptide is GREDV and the surface is a glass surface.

43. The method of claim 41 wherein the peptide is attached at the N-terminus of the peptide to the surface, wherein said surface excludes the attachment of platelets.

44. The method of claim 41 wherein the surface comprises a material selected from the group consisting of:
a ceramic;
a polymer; and
a metal.

45. A method for enhancing endothelial cell adhesion and spreading to a surface comprising chemically derivatizing the surface with a peptide consisting essentially of GREDV whereby the peptide is covalently bound to the surface through the N-terminal glycine of the peptide; and contacting the derivatized surface with a population of cells containing endothelial cells.

46. A method for enhancing fibroblast adhesion to a surface comprising chemically derivatizing the surface with a peptide consisting essentially of GYIGSR whereby the peptide is covalently bound to the surface through the N-terminal glycine of the peptide; and contacting the derivatized surface with a population of cells containing fibroblasts.

47. A cell culture substrate comprising a surface with a covalently linked peptide at a concentration density of less than about 50 picomoles/cm$^2$, said peptide being attached through an N-terminal glycine to hydroxyl groups at the substrate surface, wherein said peptide is at least one peptide selected from the of peptides group consisting of:
GRGD; GYIGSRY; GRGDF; GRGDY; GREDV; GYIGSR; GREDVY; and
wherein said substrate is capable of supporting cell focal adhesion formation and cell spreading.

48. The cell culture substrate of claim 47 wherein the peptide is GRGDY.

49. A method of preparing a cell substrate surface comprising:
covalently attaching a GRGD, GRGDY, GYIGSR, or GYIGSRY peptide through the N-terminal glycine to surface hydroxyl moieties of a substrate surface; and
plating cells on the substrate surface,
wherein the peptide is at a concentration of between about 0.001 picomoles/cm$^2$ to about 50 picomoles/cm$^2$ on the substrate surface supports cell focal adhesion formation and cell spreading.

50. A method for promoting selective endothelial cell and fibroblast cell adhesion without platelet adhesion to a surface comprising:
covalently attaching GYIGSR or GYIGSRY peptide to surface hydroxyl groups; and
exposing the surface to a population of cells that includes endothelial cells, wherein said surface supports the selective adhesion of endothelial cells and fibroblast cells and excludes platelet adhesion.

51. A method for promoting selective endothelial cell and fibroblast cell adhesion without platelet adhesion to a surface comprising;
   covalently attaching the peptide GPDSGRY through the N-terminal amine to a surface hydroxyl group; and
   exposing the surface to a population of cells that includes endothelial cells,
   wherein said surface supports the selective adhesion of endothelial cells and fibroblast cells and excludes platelet adhesion.

52. A surface for the selective adhesion of endothelial cells and fibroblast cells without platelet adhesion comprising a surface with a covalently attached GYIGSR peptide, wherein said peptide is attached through the N-terminal amine to a hydroxyl group on the surface and wherein said surface supports the selective adhesion of endothelial cells and fibroblast cells and excludes platelet adhesion.

53. A surface for the selective adhesion of endothelial cells and fibroblasts without platelet adhesion comprising a surface with a covalently attached peptide, GPDSGRY, wherein said peptide is attached through the N-terminal amine to hydroxyl groups on the surface, and wherein said surface supports the selective adhesion of endothelial cells and fibroblast cells and excludes platelet adhesion.

54. A method for promoting selective endothelial cell adhesion without fibroblast or platelet adhesion to a surface comprising:
   covalently attaching the peptide GREDVY through the N-terminal amine to a surface hydroxyl group; and
   exposing the substrate to a population of cells that includes endothelial cells,
   wherein said surface supports the selective adhesion of endothelial cells excludes fibroblast and platelet adhesion.

55. A surface for the selective adhesion of endothelial cells without fibroblast or platelet adhesion comprising a surface with a covalently attached peptide GREDVY, wherein said peptide is attached through the N-terminal amine to a hydroxyl group on the surface, and wherein said surface supports the selective adhesion of endothelial cells and excludes fibroblast and platelet adhesion.

56. A cell culture modification method comprising:
   activating hydroxyl moieties of a poly (hydroxyethyl methyl acrylate) surface of a substrate; and
   covalently coupling GRGD peptides through their N-terminal amine to hydroxyl groups of the surface of the substrate,
   wherein the GRGD peptides are included at a concentration density of between about 0.001 picomoles/cm$^2$ to about 50 picomoles/cm$^2$, and wherein the surface is capable of supporting cell focal adhesion formation and cell spreading.

57. A method of derivatizing a substrate surface to support cell focal adhesion formation and cell spreading comprising:
   chemically derivatizing a surface with GREDVY peptides, wherein said peptides are covalently attached through their N-terminal amines to hydroxyl groups on the substrate surface; and
   plating cells on the peptide derivatized surface,
   wherein the GREDVY peptide is included at a concentration density of between about 0.001 picomoles/cm$^2$ and about 50 picomoles/cm$^2$, and wherein said surface is capable of supporting cell focal adhesion formation and cell spreading.

* * * * *

UNITED STATES PATENT AND TRADEMARK OFFICE
CERTIFICATE OF CORRECTION

PATENT NO. : 5,330,911
DATED : July 19, 1994
INVENTOR(S) : Jeffrey A. Hubbell, Stephen P. Massia and Neil P. Desai It is certified that error appears in the above-indentified patent and that said Letters Patent is hereby corrected as shown below:

In claim 15, column 46, line 32, delete "methacrylate" and insert --methylacrylate-- therefor.

In claim 22, column 46, line 57, after 'of', insert --between-- therefor.

In claim 39, column 47, line 58, delete "of" and insert --is-- therefor.

In claim 41, column 48, line 8, after 'GREDV', delete ",".

In claim 45, column 48, line 27, after 'GREDV', insert --,-- therefor.

In claim 46, column 48, line 33, after 'GYIGSR', insert --,-- therefor.

UNITED STATES PATENT AND TRADEMARK OFFICE
CERTIFICATE OF CORRECTION

PATENT NO. : 5,330,911

DATED : July 19, 1994

INVENTOR(S) : Jeffrey A. Hubbell, Stephen P. Massia and Neil P. Desai

It is certified that error appears in the above-indentified patent and that said Letters Patent is hereby corrected as shown below:

In claim 47, column 48, line 43, delete "of peptides group" and insert --group of peptides-- therefor.

In claim 49, column 48, line 60, delete "on" and insert --and-- therefor.

In claim 54, column 50, line 4, after 'cells' insert --and-- therefor.

Signed and Sealed this

Twenty-fifth Day of October, 1994

Attest:

BRUCE LEHMAN

Attesting Officer    Commissioner of Patents and Trademarks